US010080779B2

(12) United States Patent
Lecron et al.

(10) Patent No.: US 10,080,779 B2
(45) Date of Patent: Sep. 25, 2018

(54) METHOD FOR INCREASING THE EXPRESSION OF ANTI-MICROBIAL PEPTIDES BY KERATINOCYTES COMPRISING ADMINISTERING A COMPOSITION COMPRISING IL-17, TNF-ALPHA AND OSM

(71) Applicants: Jean-Claude Lecron, Bonnes (FR); Hughes Gascan, Angers (FR); Franck Morel, Savigney l'Evescault (FR); Sylvie Chevalier, Angers (FR); Francois-Xavier Bernard, Saint Maurice la Clouere (FR); Katia Boniface, Mountain View, CA (US); Caroline Diveau, Palo Alto, CA (US)

(72) Inventors: Jean-Claude Lecron, Bonnes (FR); Hughes Gascan, Angers (FR); Franck Morel, Savigney l'Evescault (FR); Sylvie Chevalier, Angers (FR); Francois-Xavier Bernard, Saint Maurice la Clouere (FR); Katia Boniface, Mountain View, CA (US); Caroline Diveau, Palo Alto, CA (US)

(73) Assignees: Universite D'Angers, Angers (FR); Universite de Poitiers, Poitiers (FR); Bioalternatives SAS, Gencay (FR)

( * ) Notice: Subject to any disclaimer, the term of this patent is extended or adjusted under 35 U.S.C. 154(b) by 0 days.

(21) Appl. No.: 14/500,373

(22) Filed: Sep. 29, 2014

(65) Prior Publication Data
US 2015/0086508 A1 Mar. 26, 2015

Related U.S. Application Data

(60) Continuation-in-part of application No. 13/283,508, filed on Oct. 27, 2011, now abandoned, which is a division of application No. 11/721,763, filed as application No. PCT/EP2005/014198 on Dec. 15, 2005, now abandoned.

(30) Foreign Application Priority Data

Dec. 15, 2004 (EP) ..................................... 04293004

(51) Int. Cl.
| | |
|---|---|
| *A61K 38/19* | (2006.01) |
| *A61K 38/20* | (2006.01) |
| *A61K 38/17* | (2006.01) |
| *A61K 38/21* | (2006.01) |
| *A61K 8/64* | (2006.01) |
| *A61Q 19/00* | (2006.01) |
| *C07K 16/28* | (2006.01) |
| *C12N 5/071* | (2010.01) |

(52) U.S. Cl.
CPC ............ *A61K 38/2006* (2013.01); *A61K 8/64* (2013.01); *A61K 38/1793* (2013.01); *A61K 38/20* (2013.01); *A61K 38/204* (2013.01); *A61K 38/217* (2013.01); *A61Q 19/00* (2013.01); *C07K 16/28* (2013.01); *C12N 5/0629* (2013.01); *C07K 2317/76* (2013.01); *C12N 2501/2306* (2013.01)

(58) Field of Classification Search
CPC ...................................................... A61K 38/00
See application file for complete search history.

(56) References Cited

U.S. PATENT DOCUMENTS

| | | | |
|---|---|---|---|
| 5,451,506 | A | 9/1995 | Shoyab |
| 5,744,442 | A | 4/1998 | Richards et al. |
| 5,874,536 | A | 2/1999 | Linsley et al. |
| 5,958,442 | A | 9/1999 | Wallace et al. |
| 6,132,759 | A | 10/2000 | Schacht et al. |
| 6,706,266 | B1 | 3/2004 | Life |
| 7,501,247 | B2 | 3/2009 | Kastelein et al. |
| 2002/0025316 | A1 | 2/2002 | Ferguson |
| 2003/0157061 | A1 | 8/2003 | Bennett |
| 2006/0188500 | A1 | 8/2006 | Leung et al. |

FOREIGN PATENT DOCUMENTS

| | | |
|---|---|---|
| EP | 0 972 521 A1 | 1/2000 |
| WO | WO 01/37874 A2 | 5/2001 |
| WO | WO 01/41820 A1 | 6/2001 |
| WO | WO 02/33083 A2 | 4/2002 |
| WO | WO 03/073981 A2 | 9/2003 |

OTHER PUBLICATIONS

Boniface K, Bernard FX, et al. (2005). "L-22 inhibits epidermal differentiation and induces proinflammatory gene expression and migration of human keratinocytes." J Immunol. Mar. 15, 2005;174(6):3695-702.

Boniface, K., C. Diveu, et al. (2007). "Oncostatin M Secreted by Skin Infiltrating T Lymphocytes is a Potent Keratinocyte Activator Involved in Skin Inflammation." J. Immunol. 178:4615-4622.

Boulton, T. G., N. Stahl, et al. (1994). "Ciliary neurotrophic factor/leukemia inhibitory factor/interleukin 6/oncostatin M family of cytokines induces tyrosine phosphorylation of a common set of proteins overlapping those induced by other cytokines and growth factors." J Biol Chem 269(15): 11648-55.

European Search Report from corresponding European Patent Application No. 04293004.0 dated Sep. 9, 2005.

European Search Report from corresponding European Patent Application No. 05822885.9 dated Dec. 10, 2007.

International Search Report and Written Opinion from corresponding International Application No. PCT/EP2005/014198 dated Jun. 7, 2006.

International Search Report and Written Opinion dated Jul. 3, 2006 for PCT/EP2005/014199 (Filed Dec. 15, 2005).

(Continued)

*Primary Examiner* — Prema Mertz
(74) *Attorney, Agent, or Firm* — Alston & Bird LLP

(57) ABSTRACT

The invention disclosed herein relates to the field of epidermal repair and skin innate immunity. More particularly, the invention concerns the use of a mix of cytokines to inhibit keratinocyte differentiation, activate skin innate immunity, increase the expression of anti-microbial peptides, and improve epidermal repair. In particular, the invention concerns compositions comprising at least IL-17, TNFα and OSM that can be formulated for topical administration for cosmetic or dermatologic use.

2 Claims, 22 Drawing Sheets

Specification includes a Sequence Listing.

(56) References Cited

OTHER PUBLICATIONS

Madsen, P., H. H. Rasmussen, et al. (1991). "Molecular cloning, occurrence, and expression of a novel partially secreted protein "psoriasin" that is highly up-regulated in psoriatic skin." J Invest Dermatol 97(4): 701-12.

Office Action from corresponding European Patent Application No. 05822885.9 dated Aug. 18, 2009.

Office Action from corresponding European Patent Application No. 05824336.1 dated Mar. 20, 2008.

Office Action from corresponding European Patent Application No. 05824336.1 dated Oct. 26, 2012.

Partial European Search Report from corresponding European Patent Application No. 04293004.0 dated Jun. 23, 2005.

Raman, O., U. B. Jensen, et al. (2003). "Platelet derived growth factor (PDGF) responsive epidermis formed from human keratinocytes transduced with the PDGF beta receptor gene." J Invest Dermatol 120(5): 742-9.

Sano, S., K. S. Chan, et al. (2005). "Stat3 links activated keratinocytes and immunocytes required for development of psoriasis in a novel transgenic mouse model." Nat Med 11(1): 43-9.

Sano, S., S. Itami, et al. (1999). "Keratinocyte-15 specific ablation of Stat3 exhibits impaired skin remodeling, but does not affect skin morphogenesis." Embo J 18(17): 4657-68.

Thorey, I. S., J. Roth, et al. (2001). "The Ca2+-binding proteins S100A8 and S100A9 are encoded by novel injury-regulated genes." J Biol Chem 276(38):358 18-25.

Alowami, S., G. Qing, et al. (2003). "Psoriasin (S100A7) expression is altered during skin tumorigenesis." BMC Dermatol 3(1): 1.

Benigni, F., G. Fantuzzi, et al. (1996). "Six different cytokines that share GP130 as a receptor subunit, induce serum amyloid A and potentiate the induction of interleukin-6 and the activation of the hypothalamus-pituitary-adrenal axis by interleukin-1." Blood 87(5): 1851-4.

Bernard, F. X., N. Pedretti, et al. (2002). "Comparison of gene expression profiles in human keratinocyte mono-layer cultures, reconstituted epidermis and normal human skin; transcriptional effects of retinoid treatments in reconstituted human epidermis." Exp Dermatol 11(1): 59-74.

Boniface K, Bernard FX, et al. (2005). "IL-22 inhibits epidermal differentiation and induces proinflammatory gene expression and migration of human keratinocytes." J Immunol. Mar. 15, 2005;174(6):3695-702.

Boniface, K., C. Diveu, et al. (2007). "Oncostatin M Secreted by Skin Infiltrating T Lymphocytes is a Potent Keratinocyte Activator Involved in Skin Inflammation." J Immunol. 178:4615-4622.

Bonifati, C., A. Mussi, et al. (1998). "Spontaneous release of leukemia inhibitory factor and oncostatin-M is increased in supernatants of short-term organ cultures from lesional psoriatic skin." Arch Dermatol Res 290(1-2): 9-13.

Boulton, T. G., N. Stahl, et al. (1994). "Ciliary neurotrophic factor/leukemia inhibitory factor/interleukin 6/oncostatin M family of cytokines induces tyrosine phosphorylation of a common set of proteins overlapping those induced by other cytokines and growth factors." J Biol Chem 269(15): 11648-55.

Broome, A. M., D. Ryan, et al. (2003). "S100 protein subcellular localization during epidermal differentiation and psoriasis." J Histochem Cytochem 51(5): 675-85.

Bullard, K. M., L. Lund, et al. (1999). "Impaired wound contraction in stromelysin-1-deficient mice." Ann Surg 230(2): 260-5.

Dillon S et al., "Transgenic Mice Overexpressing a Novel Cytokine (IL-31) Develop a Severe Pruritic Skin Phenotype Resembling Atopic Dermatitis" Eur. Cytokine Netw. vol. 14, Suppl. 3, Sep. 2003; p. 81; XP009067737.

Dillon, S. R., C. Sprecher, et al. (2004). "Interleukin 31, a cytokine produced by activated T cells, induces dermatitis in mice." Nat Immunol 5(7): 752-60.

Diveu, C. A.H. Lak-Hal, et al. (2004). "Predominant expression of the long isoform of GP130-like (GPL) receptor is required for interleukin-31 signaling"; Eur Cytokin Netw 15(4): 291-302.

Donato, R. (1999). "Functional roles of S100 proteins, calcium-binding proteins of the EF-hand type." Biochim Biophys Acta 1450(3): 191-231.

Gallucci, R. M., D. K. Sloan, et al. (2004). "Interleukin 6 indirectly induces keratinocyte migration." J Invest Dermatol 122(3): 764-72.

Gallucci, R. M., P. P. Simeonova, et al. (2000). "Impaired cutaneous wound healing in interleukin-6-deficient and immunosuppressed mice." Faseb J 14(15): 2525-31.

Gebhardt, C., U. Breitenbach, et al. (2002). "Calgranulins S100A8 and S100A9 are negatively regulated by glucocorticoids in a c-Fos-dependent manner and overexpressed throughout skin carcinogenesis." Oncogene 21(27): 4266-76.

Glaser, R., J. Harder, et al. (2005). "Antimicrobial psoriasin (S100A7) protects human skin from *Escherichia coli* infection." Nat Immunol 6(1): 57-64.

Guenou H, Nissan X, Larcher F, Feteira J, Lemaitre G, et al. (2009) Human embryonic stem-cell derivatives for full reconstruction of the pluristratified epidermis: a preclinical study. Lancet 374: 1745-1753.

Harder, J., J. Bartels, et al. (1997). "A peptide antibiotic from human skin." Nature 387(6636): 861.

Ihn, H. and K. Tamaki (2000). "Oncostatin M stimulates the growth of dermal fibroblasts via a mitogen-activated protein kinase-dependent pathway." J Immunol 165(4): 2149-55.

Jonak, C., G. Klosner, et al. (2002). "Subcorneal colocalization of the small heat shock protein, hsp27, with keratins and proteins of the cornified cell envelope." Br J Dermatol 147(1): 13-9.

Kira, M., S. Sano, et al. (2002). "STAT3 deficiency in keratinocytes leads to compromised cell migration through hyperphosphorylation of p130(cas)." J Biol Chem 277(15): 12931-6.

Koch, A. E., S. L. Kunkel, et al. (1994). "Epithelial neutrophil activating peptide-78: A novel chemotactic cytokine for neutrophils in arthritis." J Clin Invest 94(3): 1012-8.

Komine, M., L. S. Rao, et al. (2000). "Inflammatory versus proliferative processes in epidermis. Tumor necrosis factor alpha induces K6b keratin synthesis through a transcriptional complex containing NFkappa B and C/EBPbeta." J Biol Chem 275(41): 32077-88.

Lew, W., A.M. Bowcock, et al. (2004). "Psoriasis vulgaris: cutaneous lymphoid tissue supports T-cell activation and "Type 1" inflammatory gene expression." Trends Immunol 25(6): 295-305.

Lugering, N., T. Kucharzik, et al. (1997). "Importance of combined treatment with IL-10 and IL-4, but not IL-13, for inhibition of monocyte release of the Ca(2+)-binding protein MRP8/14." Immunology 91(1): 130-4.

Madsen, P., H. H. Rasmussen, et al. (1991). "Molecular cloning, occurrence, and expression of a novel partially secreted protein "psoriasis" that is highly up-regulated in psoriatic skin." J Invest Dermatol 97(4): 701-12.

Mehul, B., D. Bernard, et al. (2000). "Identification and cloning of a new calmodulin-like protein from human epidermis." J Biol Chem 275(17): 12841-7.

Mehul, B., D. Bernard, et al. (2001). "Calmodulin-like skin protein: a new marker of keratinocyte differentiation." J Invest Dermatol 116(6): 905-9.

Nagase, H. and J. F. Woessner, Jr. (1999). "Matrix metalloproteinases." J Biol Chem 274(31): 21491-4.

Navarro, J. M., J. Casatorres, et al. (1995). "Elements controlling the expression and induction of the skin hyperproliferation-associated keratin K6." J Biol Chem 270(36): 21362-7.

Nizet, V., T. Ohtake, et al. (2001). "Innate antimicrobial peptide protects the skin from invasive bacterial infection." Nature 414(6862): 454-7.

Nomura, I., E. Goleva, et al. (2003). "Cytokine milieu of atopic dermatitis, as compared to psoriasis, skin prevents induction of innate immune response genes." J Immunol 171(6): 3262-9.

Ong, P. Y., T. Ohtake, et al. (2002). "Endogenous antimicrobial peptides and skin infections in atopic dermatitis." N Engl J Med 347(15): 1151-60.

Paglia, D., S. Kondo, et al. (1996). "Leukaemia inhibitory factor is expressed by normal human keratinocytes in vitro and in vivo." Br J Dermatol 134(5): 817-23.

(56) References Cited

OTHER PUBLICATIONS

Paramio, J. M., M. L. Casanova, et al. (1999). "Modulation of cell proliferation by cytokeratins K10 and K16." Mol Cell Biol 19(4): 3086-94.
Pattyn, F., F. Speleman, et al. (2003). "RTPrimerDB: the real-time PCR primer and probe database." Nucleic Acids Res 31(1): 122-3.
Pfaffl, M. W. (2001). "A new mathematical model for relative quantification in real-time RT-PCR." Nucleic Acids Res 29(9): e45.
Pfaffl, M. W., G. W. Horgan, and L. Dempfle. (2002). "Relative expression software tool (REST) for group-wise comparison and statistical analysis of relative 25 expression results in real-time PCR". Nucleic Acids Res 30:e36.
Phoenix, David et al.; Antimicrobial Peptides, First Edition, Chapter 1—Antimicrobial Peptides: Their History, Evolution, and Functional Promiscuity; 2013 Wiley-VCH Verlag GmbH & Co.
Pilcher, B. K., M. Wang, et al. (1999). "Role of matrix metalloproteinases and their inhibition in cutaneous wound healing and allergic contact hypersensitivity." Ann N Y Acad Sci 878: 12-24.
Rogers, M. S., T. Kobayashi, et al. (2001). "Human calmodulin-like protein is an epithelial-specific protein regulated during keratinocyte differentiation." Exp Cell Res 267(2): 2 16-24.
Rollman, O., U. B. Jensen, et al. (2003). "Platelet derived growth factor (PDGF) responsive epidermis formed from human keratinocytes transduced with the PDGF beta receptor gene." J Invest Dermatol 120(5): 742-9.
Rosdy, M., B. Bertino, et al. (1997). "Retinoic acid inhibits epidermal differentiation when applied topically on the stratum corneum of epidermis formed in vitro by human keratinocytes grown on defined medium." In Vitro Toxicology 10(1): 39-47.
Roth, J., T. Vogl, et al. (2003). "Phagocyte-specific S100 proteins: a novel group of proinflammatory molecules." Trends Immunol 24(4): 155-8.
Ryckman, C., K. Vandal, et al. (2003). "Proinflammatory activities of S 100: proteins S100A8, S100A9, and S100A8/A9 induce neutrophil chemotaxis and adhesion." J Immunol 170(6): 3233-42.
Sa SM, Valdez PA, Wu J, Jung K, Zhong F, et al. (2007) The effects of IL-20 subfamily cytokines on reconstituted human epidermis suggest potential roles in cutaneous innate defense and pathogenic adaptive immunity in psoriasis. J Immunol 178: 2229-2240.
Sano, S., K. S. Chan, et al. (2005). "Stat3 links activated keratinocytes and immunocytes required for development of psoriasis in a novel trangenic mouse model." Nat Med 11(1): 43-9.
Sano, S., S. Itami, et al. (1999). "Keratinocyte-15 specific ablation of Stat3 exhibits impaired skin remodeling, but does not affect skin morphogenesis." Embo J. 18(17): 4657-68.
Sugawara, T., R. M. Gallucci, et al. (2001). "Regulation and role of interleukin 6 in wounded human epithelial keratinocytes." Cytokine 15(6): 328-36.
Taga, T. and T. Kishimoto (1997). "Gp130 and the interleukin-6 family of cytokines." Annu Rev Immunol 15: 797-8 19.
Thorey, I. S., J. Roth, et al. (2001). "The Ca2+-binding proteins S100A8 and S100A9 are encoded by novel injury-regulated genes." J Biol Chem 276(38): 358.
Trickett, A. and Y.L. Kwan (2003). "T cell stimulation and expansion using anti-CD3/CD28 beads." J Immunol Methods 275(1-2): 251-5.
Vandesompele, J., K. De Preter, et al. (2002). "Accurate normalization of real-time quantitative RT-PCR data by geometric averaging of multiple internal control genes." Genome Biol 3(7): RESEARCH0034.
Wagener, F. A., H. E. van Beurden, et al. (2003). "The heme-heme oxygenase system: a molecular switch in wound healing." Blood 102(2): 52 1-8.
Wahl, A. F. and P. M. Wallace (2001). "Oncostatin M in the anti-inflammatory response." Ann Rheum Dis 60 Suppi 3: iii75-80.
Watson, P.H., E. R. Leygue, et al. (1998). "Psoriasin (S100A7)." Int J Biochem Cell Biol 30(5): 567-71.
Yssel, H., S. Lecart, et al. (2001). "Regulatory T cells and allergic asthma." Microbes Infect 3(11): 899-904.
Yu, J. Y., S. L. DeRuiter, et al. (2002). "RNA interference by expression of short-interfering RNAs and hairpin RNAs in mammalian cells." Proc Natl Acad Sci U S A 99(9): 6047-52.

METHOD FOR INCREASING THE EXPRESSION OF ANTI-MICROBIAL PEPTIDES BY KERATINOCYTES COMPRISING ADMINISTERING A COMPOSITION COMPRISING IL-17, TNF-ALPHA AND OSM

CROSS-REFERENCE TO RELATED APPLICATIONS

The present application is a continuation-in-part of U.S. application Ser. No. 13/283,508, which was filed Oct. 27, 2011, which is a divisional of U.S. application Ser. No. 11/721,763, now abandoned, which received a filing date of Feb. 4, 2008, which is a national stage application filed under 35 U.S.C. § 371 of International Application No. PCT/EP2005/014198, filed Dec. 15, 2005, which claims priority from European Patent Application No. 04293004.0, filed Dec. 15, 2004, each of which is incorporated by reference in its entirety.

FIELD OF THE INVENTION

The invention disclosed herein relates to the field of epidermal repair and skin innate immunity. More particularly, the invention concerns the use of a mix of cytokines to inhibit keratinocyte differentiation, activate skin innate immunity and improve epidermal repair.

BACKGROUND OF THE INVENTION

The skin is a large and complex tissue providing a protective interface between an organism and its environment. Epidermis forms its external surface, and is mainly constituted of multiple layers of specialized epithelial cells named keratinocytes. Skin can be injured by many different causes, including micro-organisms, chemicals, behaviours, physical injury, ageing, U.V. irradiation, cancer, autoimmune or inflammatory diseases.

Epidermis homeostasis is regulated by a balance between differentiation and proliferation of keratinocytes, differentiating from the basal to the cornified layers of the skin. In response to epidermal stress or in some skin diseases, this equilibrium is broken. Keratinocytes become able to differentially respond to soluble mediators such as Epidermal Growth Factor (EGF) family members, and to additional growth factors and cytokines (FGFs, IGF-1, PDGF, HGF, TGFβ family members, GM-CSF, TSLP, IL-1, TNF-α). These modulators are produced by the keratinocytes themselves, the skin fibroblasts, the Langerhans cells or by immune infiltrating cells such as T lymphocytes. In response, the keratinocytes release additional signaling molecules, modulate the expression level of cell surface receptors, modify their cytoskeleton morphology, and modulate their migration, differentiation and proliferation capacities. These changes are associated with an inflammatory response, leading to either wound healing or to a chronic disease.

The cytokines of the IL-6 family are multifunctional proteins regulating cell growth and differentiation in a large number of biological systems, such as immunity, hematopoiesis, neural development, reproduction, bone modeling and inflammatory processes. This cytokine family encompasses nine different members: IL-6, IL-11, IL-27, leukemia inhibitory factor (LIF), cardiotrophin-1, cardiotrophin-like factor, ciliary neurotrophic factor, neuropoietin, and oncostatin M (OSM). The activities of theses cytokines are mediated through ligand-induced oligomerization of a dimeric or trimeric receptor complex. The IL-6 family of cytokines shares the gp130 receptor subunit in the formation of their respective heteromeric receptors (Taga and Kishimoto 1997). A recently described cytokine, named IL-31, has been classified by Dillon et al as a novel member of the gp130-IL6 family, because its receptor is a heterodimer comprising gp130-like type I cytokine receptor (GPL) and an OSMR subunit (Dillon, Sprecher et al. 2004).

Different publications have reported that some members of the IL-6 family may be implicated in certain skin diseases and wound healing processes. IL-6, IL-11, LIF and OSM have been found to be increased in psoriatic lesions (Bonifati, Mussi et al. 1998), and IL-6 and LIF are produced by purified keratinocytes (Paglia, Kondo et al. 1996; Sugawara, Gallucci et al. 2001). An impaired wound healing process has been reported in IL-6 and STAT3 deficient mice (Sano, Itami et al. 1999; Gallucci, Simeonova et al. 2000). However, further studies on cultured keratinocytes isolated from IL-6 deficient mice showed that the action of IL-6 on keratinocyte migration is mediated by dermal fibroblasts. Indeed, IL-6 alone did not significantly modulate the proliferation or migration of said IL-6-deficient keratinocytes, whereas IL-6 significantly induced their migration when co-cultured with dermal fibroblasts (Gallucci, Sloan et al. 2004).

OSM is secreted from activated T cells, monocytes stimulated by cytokines and from dendritic cells. OSM is a pro-inflammatory mediator, which strongly triggers protein synthesis in hepatocytes (Benigni, Fantuzzi et al. 1996). In humans, OSM and LIF display overlapping biological functions in a number of tissues by increasing growth regulation, differentiation, gene expression, cell survival. OSM is also known to elicit some unique biological functions, not shared with LIF, such as growth inhibition of some tumor cell lines or stimulation of AIDS-associated Kaposi's sarcoma cells. These shared and specific functions of OSM are explained by the existence of two types of OSM receptor complexes. Beside the common LIF/OSM receptor complex made of gp130/LIFRβ subunits, OSM is also able to specifically recognize a type II receptor associating gp130 with OSMRβ (also referred to as "OSMR" or "OSM-R"), which is expressed by endothelial cells, hepatic cells, lung cells, fibroblasts, hematopoietic cells and by some tumor cell lines. The subsequent signaling cascade involves activation of the Janus kinase (JAK 1, JAK 2, Tyk 2), followed by an activation of the Signal Transducer and Activator of Transcription (STAT1, STAT3) and of the Map kinase pathways.

In addition to its anti-neoplastic activity and its role in the pro-inflammatory response (Wahl and Wallace 2001); Shoyab et al, U.S. Pat. No. 5,451,506; Richards et al., U.S. Pat. No. 5,744,442), OSM has been described as stimulating the growth of dermal fibroblasts via a MAP kinase-dependent pathway, thereby promoting dermal wound healing (Ihn and Tamaki 2000).

Other cytokines are also known to have an effect on dermis. For example, Dillon et al (supra) suggest that overexpression of IL-31 may be involved in promoting the dermatitis and epithelial responses that characterize allergic and non-allergic diseases. These authors do not suggest to use IL-31 for promoting skin repair.

When skin is injured, its complete repair implies that both the dermis and the epidermis are repaired. Healing of epidermis and dermis, which comprise different cell-types, involve different mechanisms.

Currently, treatments for improving skin healing mainly target the dermis. However, epidermis reconstitution is necessary for a complete recovering. In some cases, for example in the case of large burns, ulcers or bedscores, physiological epidermal healing processes are not efficient enough for restoring the protecting function of skin. In such cases, it is necessary to rapidly cover the damaged area, to avoid infections and possibly dehydration. It is also necessary to stimulate epidermis regeneration. In the case of severe burns on less than half of the body surface, skin auto-graft is performed after excision of the burnt skin. To that aim, sane skin is taken from the patient and mechanically treated for increasing its surface. This "wick-skin" is then grafted on the lesions. When the burnt surface is too large (more than half of the body surface), this process is not feasible. It is then necessary to temporarily cover the wounds to avoid dehydration and infection. This is currently performed with either skin from cadavers, or with skin substitutes such as acellular dressings like tulle gras, possibly incorporating growth factors for improving wound healing. Examples of such skin substitutes are described in U.S. Pat. No. 6,132,759 or in WO 01/41820. In parallel, skin cells from the patient are expanded in vitro, in order to obtain epithelial layers that are then grafted. One to 2 m² can be obtained in 3 weeks, from a few cm² of sane skin. However, these techniques are long, costly, and need a heavy infrastructure to be successfully performed. Hence it is clear that there exists a real need for novel dermatological approaches for improving epidermal repair. Enhancing centripetal migration of the keratinocytes would clearly accelerate/enable healing and re-epithelialization. Acting on the keratinocytes' differentiation and migration is also necessary for treating specific diseases such as bullous epidermolysis. The phrase "bullous epidermolysis" designates a number of dermatitis of different origins (such as bleds, burns, autoimmune diseases, . . . ), leading to a detachment of the epidermis and liquid accumulation between dermis and epidermis. A particular example of bullous epidermolysis is bullous phemphigoid.

Improving epidermal repair is also important in the cosmetic field, where no efficient compositions exist for improving the aspect of scars, originating either from recent small wounds or from old cuts, spots, stretch marks and the like.

SUMMARY OF THE INVENTION

A first object of the present invention is a method for improving epidermal repair and/or cutaneous innate immunity, comprising administering IL-1α, IL-17 and TNFα to a patient in need thereof. According to a preferred embodiment, oncostatin M (OSM) and/or IL-22 are also administered to the patient, either simultaneously or sequentially.

The method according to the present invention is useful, inter alia, for promoting epidermal healing, for promoting keratinocyte migration for increasing epidermal thickness, for preventing and/or attenuating chaps on hands, lips, face or body, for preventing and/or attenuating stretch marks, for improving the aspect and comfort of scars and for improving the aspect and comfort of epidermal wounds during their cicatrisation.

The present invention also pertains to a method for increasing the expression of anti-microbial peptides by keratinocytes, comprising contacting said keratinocytes with a composition comprising IL-1α, IL-17, TNFα, IL-22 and OSM.

Another aspect of the present invention is a composition comprising IL-1α, IL-17 and TNFα. In some embodiments, the composition further comprises IL-22 and/or OSM.

Such compositions can be used for promoting keratinocyte migration, or for promoting epidermal healing. They can also be used for preventing, attenuating or treating bullous epidermolysis. The compositions according to the invention can also be used for increasing epidermal thickness, either in vivo or in vitro.

According to specific embodiments of the present invention, a mix of cytokines as described above is used for the preparation of a composition for preventing and/or attenuating chaps on hands, lips, face or body, or for preventing and/or attenuating stretch marks. Other applications of the compositions according to the invention are the improvement of the aspect and comfort of scars, and/or the improvement of the aspect and comfort of epidermal wounds during their healing.

(A) Total RNA was extracted from NHEK of 4 independent donors. RT-PCR was performed with specific primers for OSMR, gp130, LIFR and GAPDH genes. Serial dilutions of cDNA were amplified to have a semi-quantitative analysis of transcripts expression level. PCR products were analysed by agarose gel electrophoresis. (B) Immunolabelling of cell surface NHEK and flux cytometry analysis. Gp130 and OSMR are clearly detected on the cell, but not the LIFR. (C) Twenty µg of cell lysate from NHEK and the glioblastoma cell line GO-G-UVM were separated by SDS-PAGE (10%) and transferred to nitrocellulose membrane. Ponceau red staining was used to control loading homogeneity. Detection of gp130, OSMR, LIFR and tubulin bands were assessed by Western blot. The results are representative of 3 independent experiments.

Figure 2:
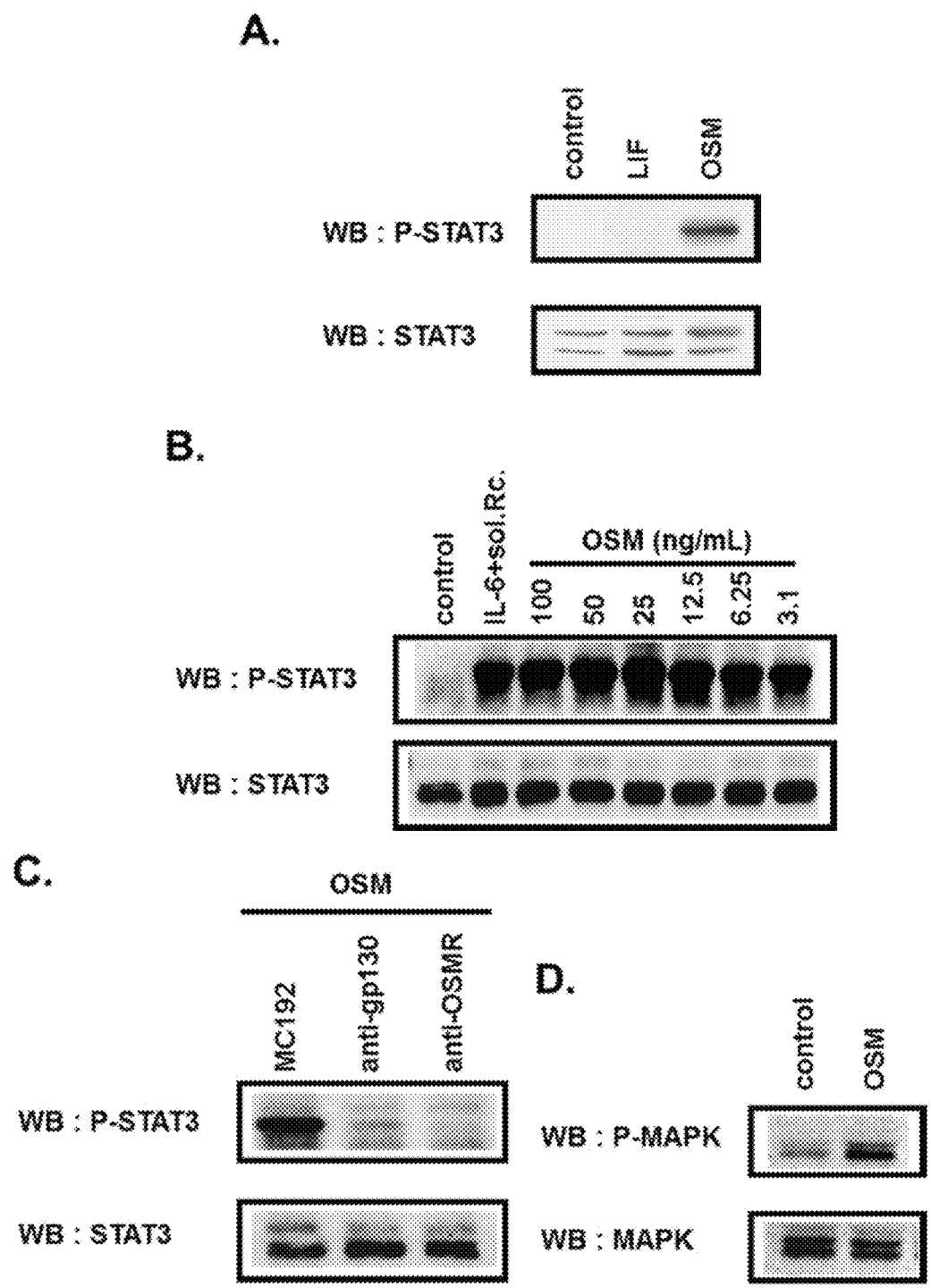

FIG. 2 shows the induction of STAT3 and MAP kinase phosphorylation by OSM in NHEK.

(A) NHEK were stimulated or not with LIF or OSM (50 ng/ml). (B) NHEK were stimulated or not for 15 min with 50 ng/ml of IL-5 (negative control) or with 100, 50, 25, 12.5, 6.25 or 3.1 ng/ml of OSM, and phospho-STAT3 (P-STAT3) and STAT3 protein levels were assessed by Western blot. Before stimulation with the cytokines, cells were incubated for 2 h in the presence of neutralizing antibodies, an anti-gp130 (AN-HH1), or an anti-OSMR (XR-M70) monoclonal antibody, or with an isotype control mAb MC192 (final antibody concentration, 15 µg/ml (C). Phospho-MAPK (P-MAPK) and MAPK protein levels in response to OSM was assessed by Western blot (D).

Figure 3:
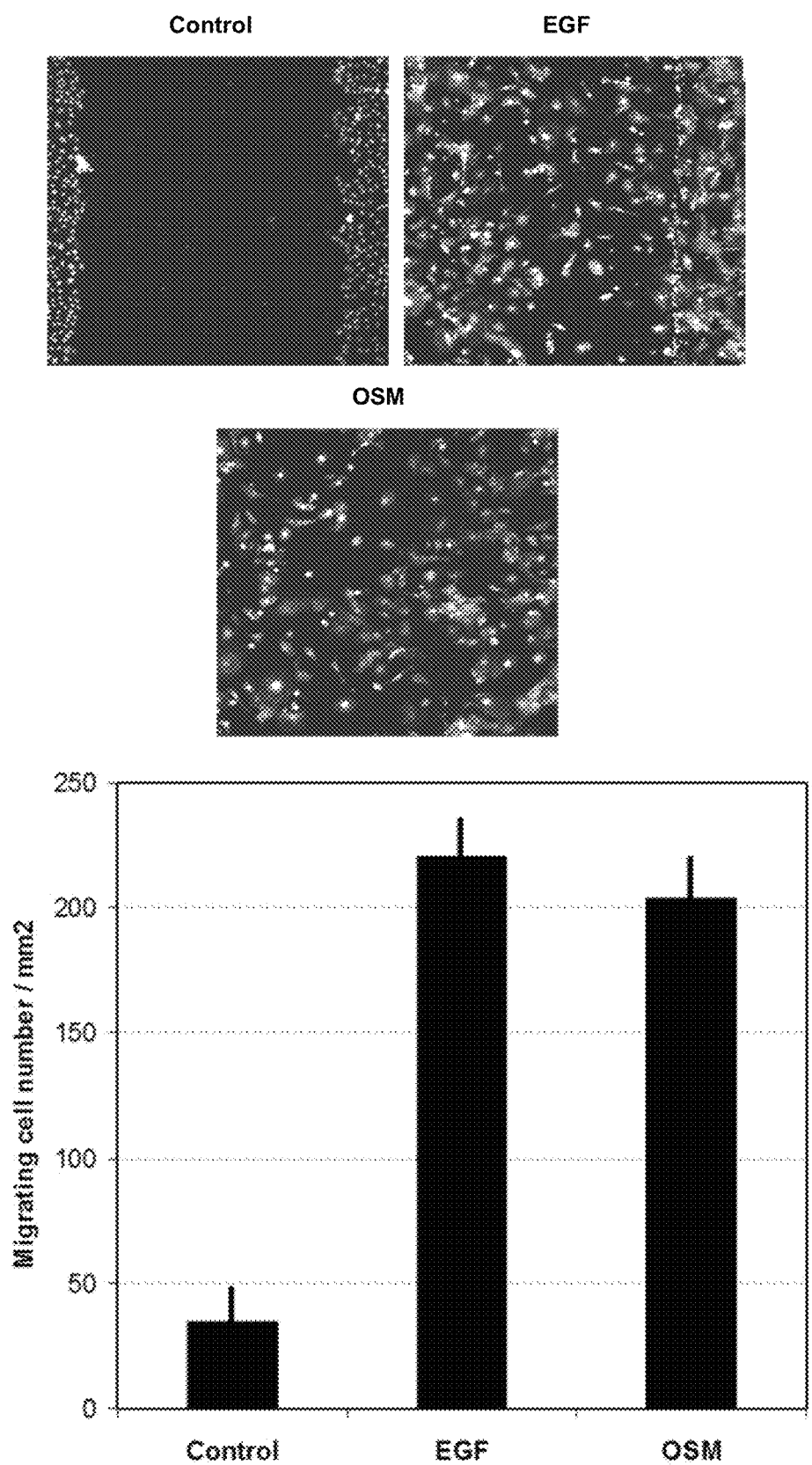

FIG. 3 shows the effect of OSM on keratinocyte migration.

In vitro wounds were introduced in mitomycin-treated confluent NHEK culture and the keratinocytes were cultured for 48 h with or without 10 ng/ml of EGF or OSM. Cell migration to the cell free area was assessed as described in Materials and Methods. Each bar represents the mean±SEM of migrating keratinocytes counted in 4 non-overlapping fields. One experiment representative of 2.

* p<0.001 compared with respective control without cytokine, based on Student's t test.

Figure 4:
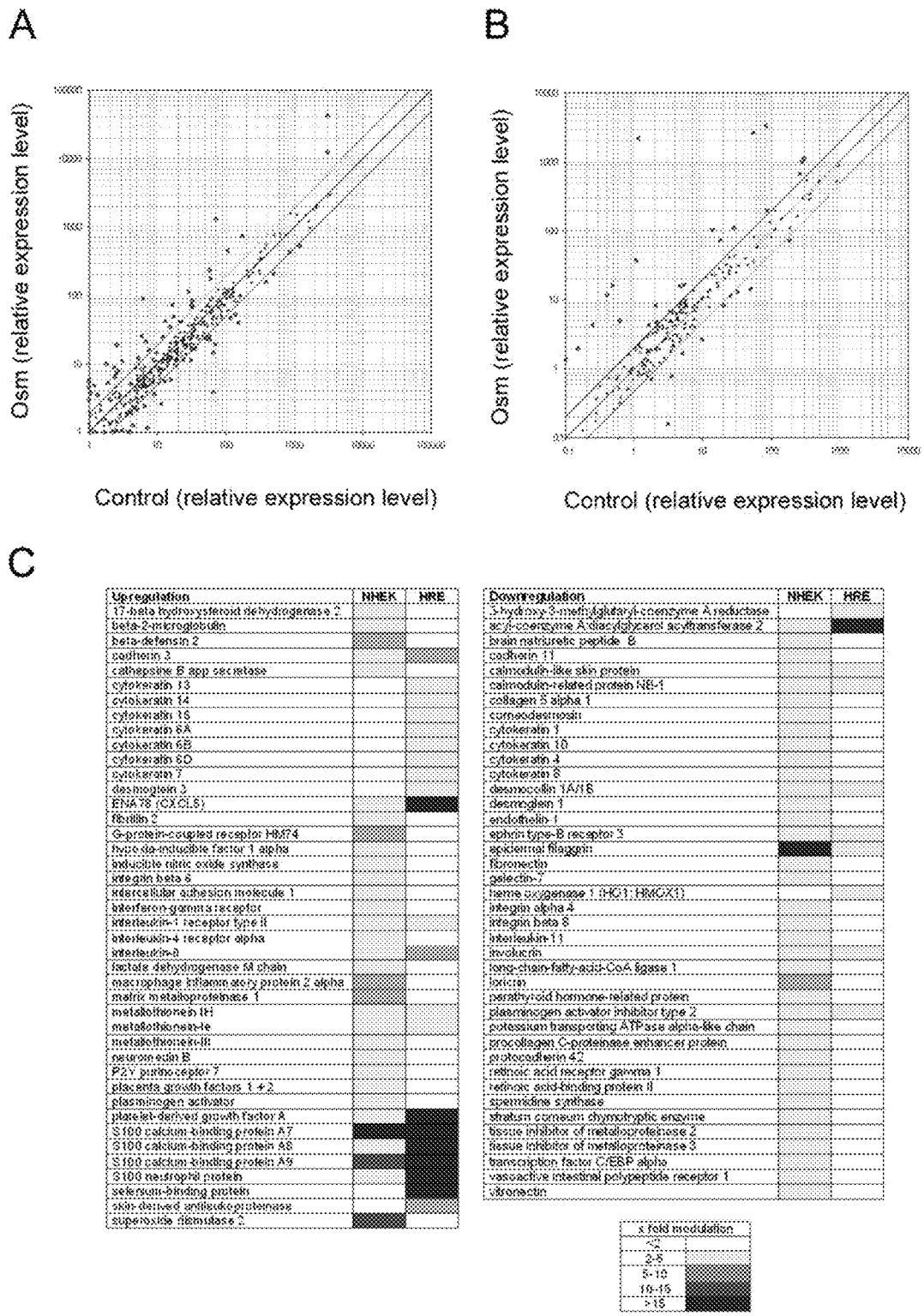

FIG. 4 shows expression profiles obtained from OSM stimulated NHEK and OSM treated RHE.

NHEK (A) or RHE (B) were cultured with or without 10 ng/ml of OSM for 24 h. Total RNA was isolated, treated with Dnase I, and used to make $^{33}$P-labelled cDNA probes, which were hybridized to cDNA arrays. The computer images were obtained after 5 days exposure to a Molecular Dynamics Storm storage screen and further scanning. After local background substraction, an average signal intensity from duplicate spots was normalized for differences in probe labelling using the values obtained for housekeeping genes. (C) The OSM-induced modulation was expressed as the percentage ratio of the signal intensities for cells treated with each cytokine over the signal intensity for unstimulated cells.

Figure 5:
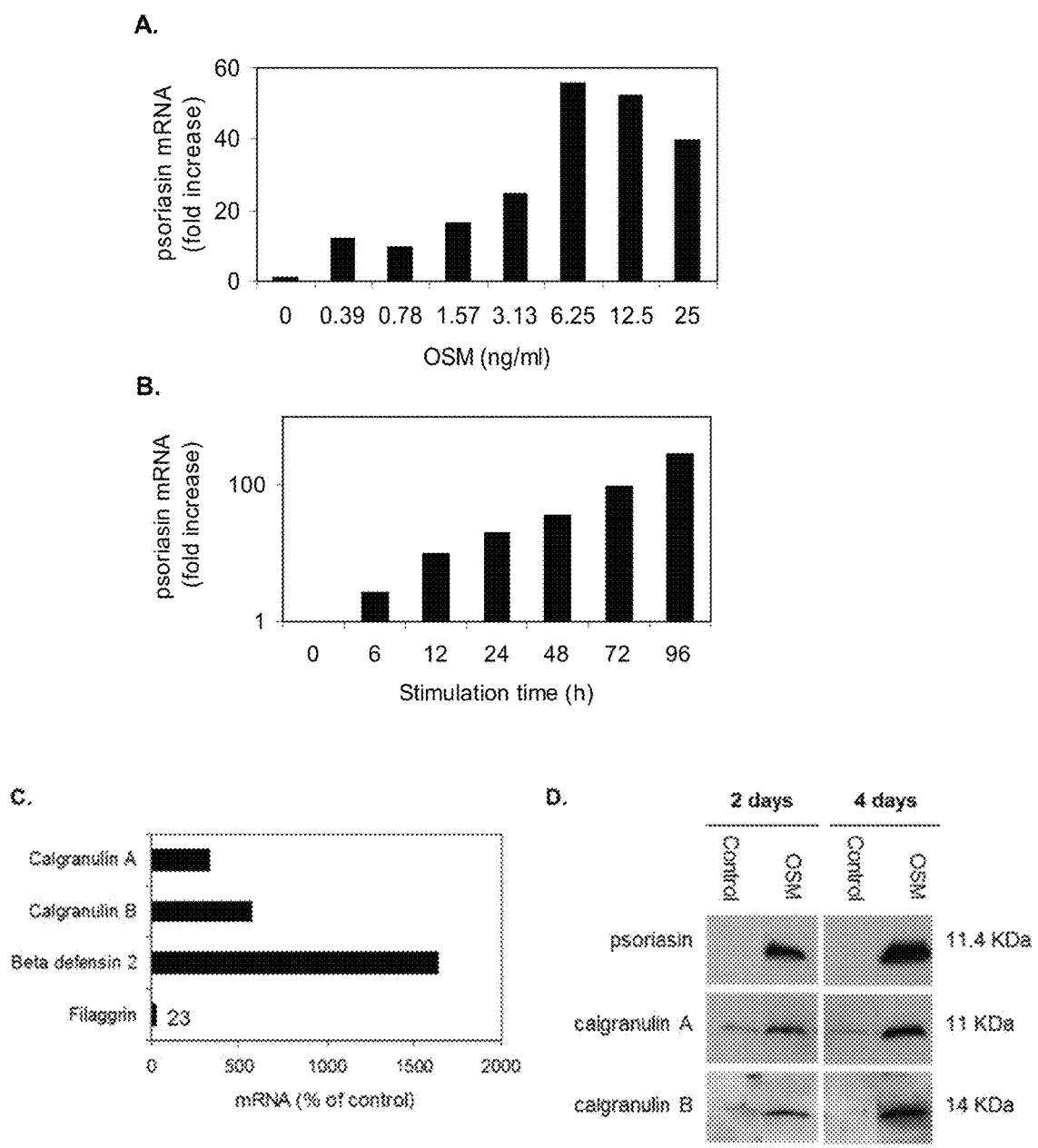

FIG. 5 shows the effect of OSM on S100A7-9 synthesis by NHEK.

NHEK were cultured with or without 0.4, 0.8, 1.6, 3.1, 6.3, 12.5 or 25 ng/ml of OSM for 48 h (A) or with or without 10 ng/ml of OSM for 6, 12, 24, 48, 72, 96 h (B). Total RNA was extracted, reverse transcribed, and S100A7 and HMBS mRNA relative expression was quantified by real time PCR. HMBS was used as a housekeeping gene to normalize gene expression as detailed in Materials and Methods. Results, expressed as the relative expression of stimulated cells over control cells, are representative of 2 independent experiments. (C) NHEK were cultured with or without 10 ng/ml of OSM for 48 h. Relative S100A8-calgranulin A, S100A9-calgranulin B, β-defensin 2 and filaggrin mRNA expression was quantified by quantitative RT-PCR. Results are expressed as the relative expression of stimulated cells over control cells. (D) NHEK were cultured with or without 10 ng/ml of OSM for 48 and 96 h. Twenty µg of cell lysate were separated by SDS-PAGE (16%) and transferred to nitrocellulose membrane. Ponceau red staining was used to control loading homogeneity. S100A7, S100A8 and S100A9 protein levels was determined by Western blot. The results are representative of 3 independent experiments.

Figure 6:
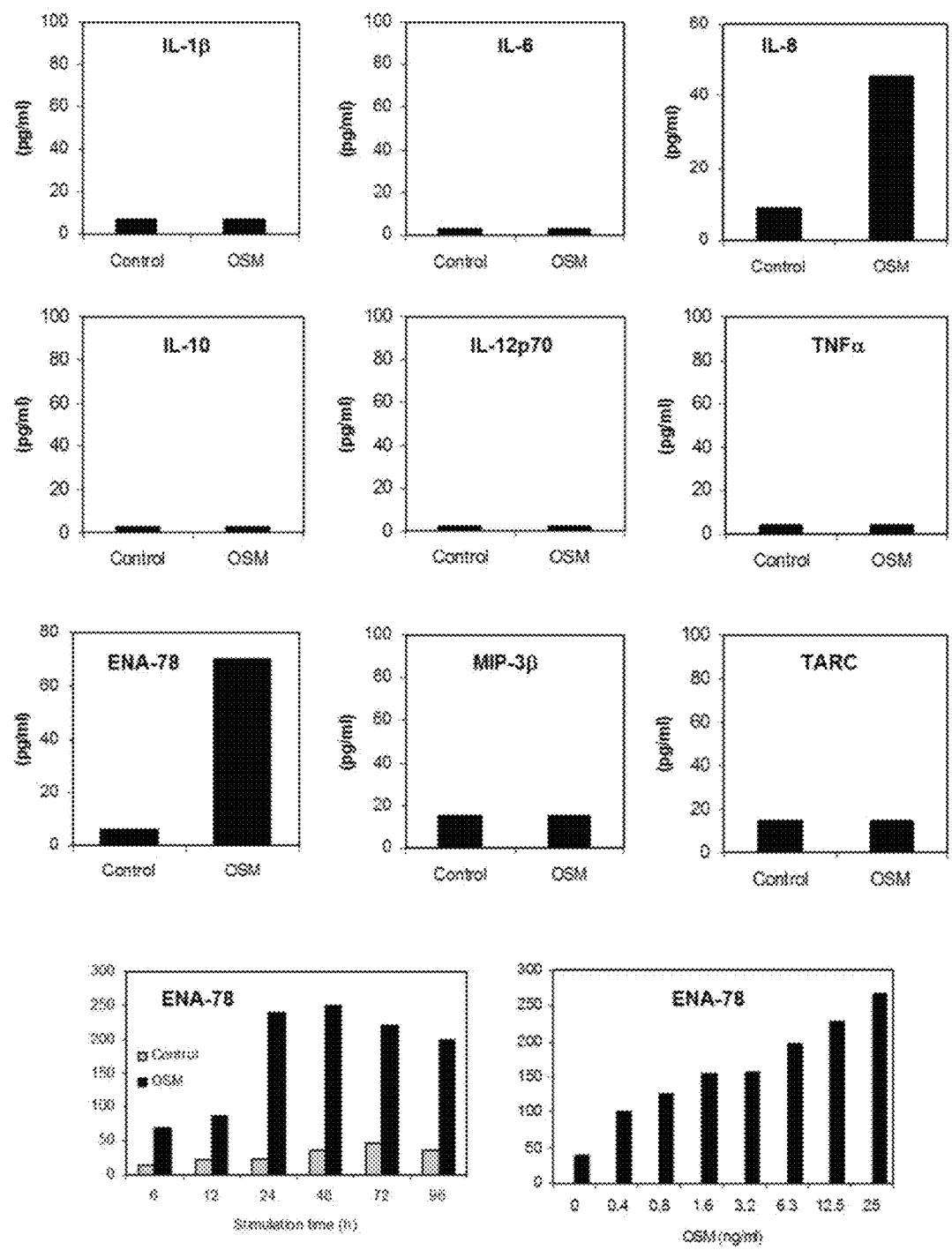

FIG. 6 shows cytokines and chemokines production by NHEK. IL-1beta, IL-6, IL-8, IL-10, IL-12p70, TNF alpha, ENA-78, MIP 3 beta were measured by specific ELISA in 48 h NHEK culture supernatants. Cells were cultured in the presence or not of OSM. Dose-response (0.4 to 25 ng/ml) and kinetic (6 to 96 h) studies of ENA78 production were also performed.

Figure 7:
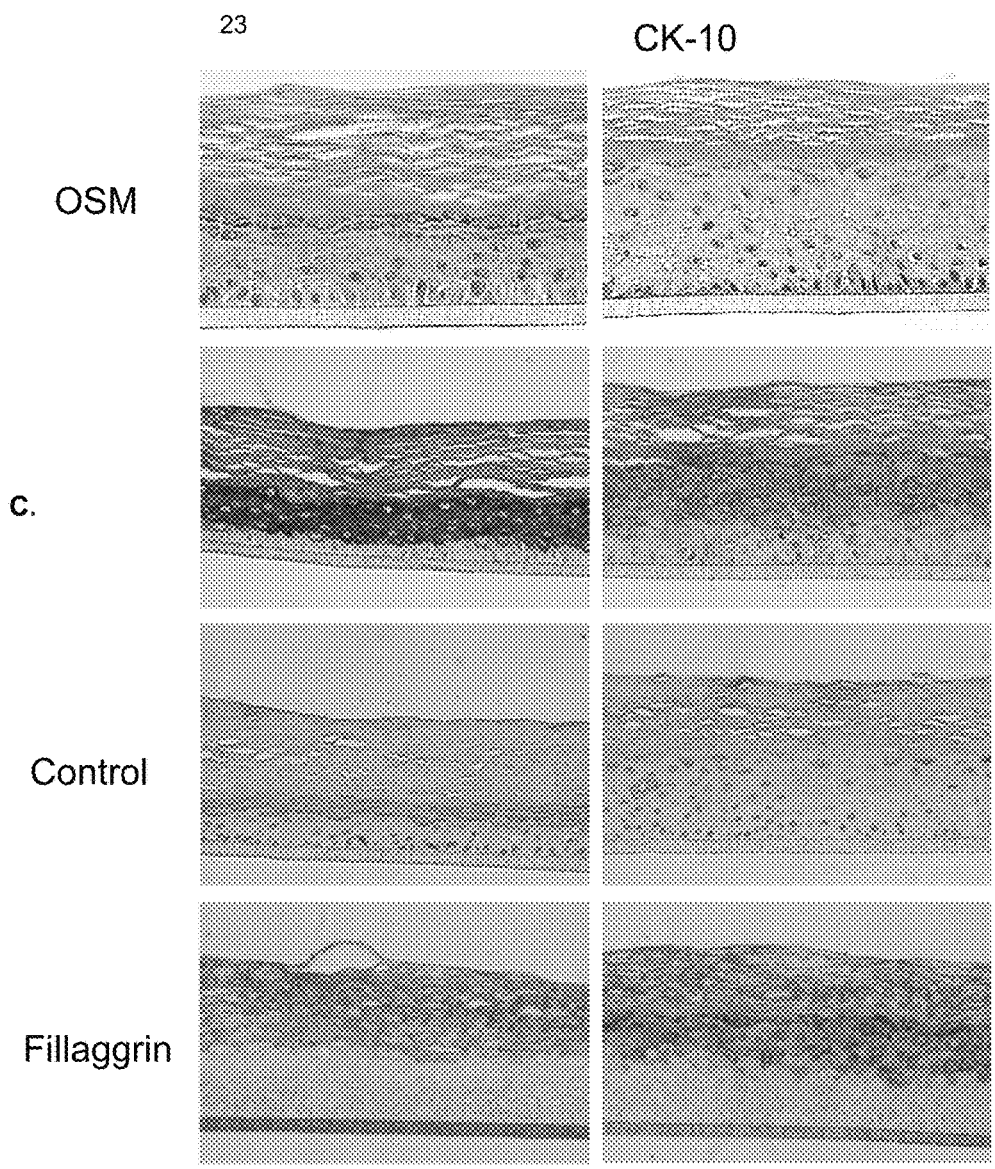

FIG. 7 shows histological and immunohistochemical analysis of RHE stimulated or not with 10 ng/ml of OSM for 4 days. RHE were fixed, embedded in paraffin. Four micron vertical sections were stained with hematoxylin/eosin or reacted with anti-K10 keratin mAb, anti-filaggrin mAb or anti-S100A7 mAb and then photographed under a microscope (magnification ×200).

Figure 8:
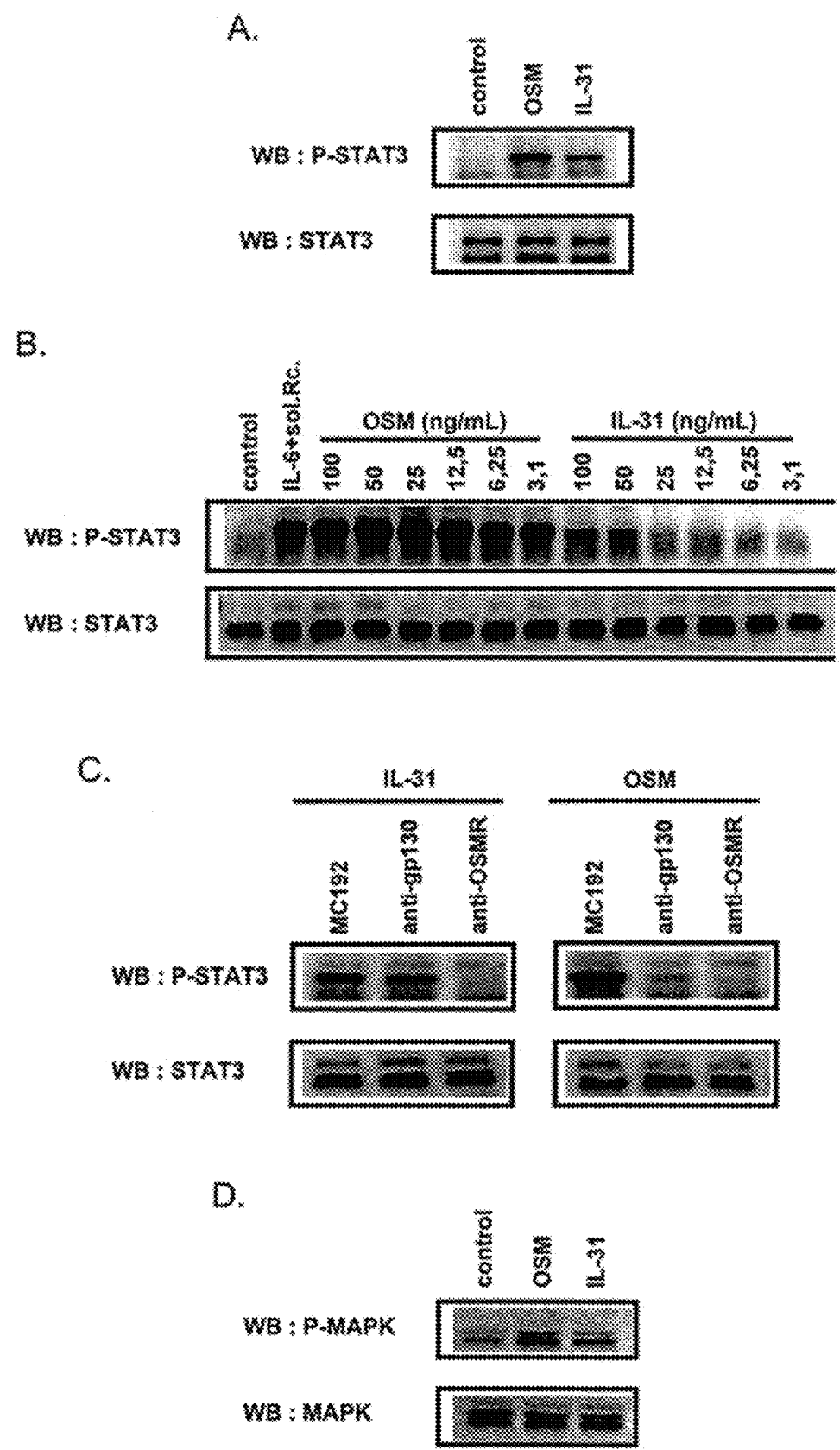

FIG. 8 shows induction of STAT3 and MAP kinase phosphorylation by IL-31 and OSM in NHEK.

NHEK were stimulated or not for 15 min with 10 ng/ml of OSM, or with 100 ng/ml of IL-31 (A), or with different concentrations of these cytokines (B), and phospho-STAT3 (P-STAT3) and STAT3 protein levels were assessed by Western blot. Before stimulation with the cytokines, cells were incubated for 2 h in the presence of neutralizing antibodies, an anti-gp130 (AN-HH1), or an anti-OSMR (XR-M70) monoclonal antibody, or with an isotype control mAb MC192 (final antibody concentration, 15 µg/ml) (C). Phospho-MAPK (P-MAPK) and MAPK protein levels in response to IL-31 and OSM was assessed by Western blot (D).

Figure 9:
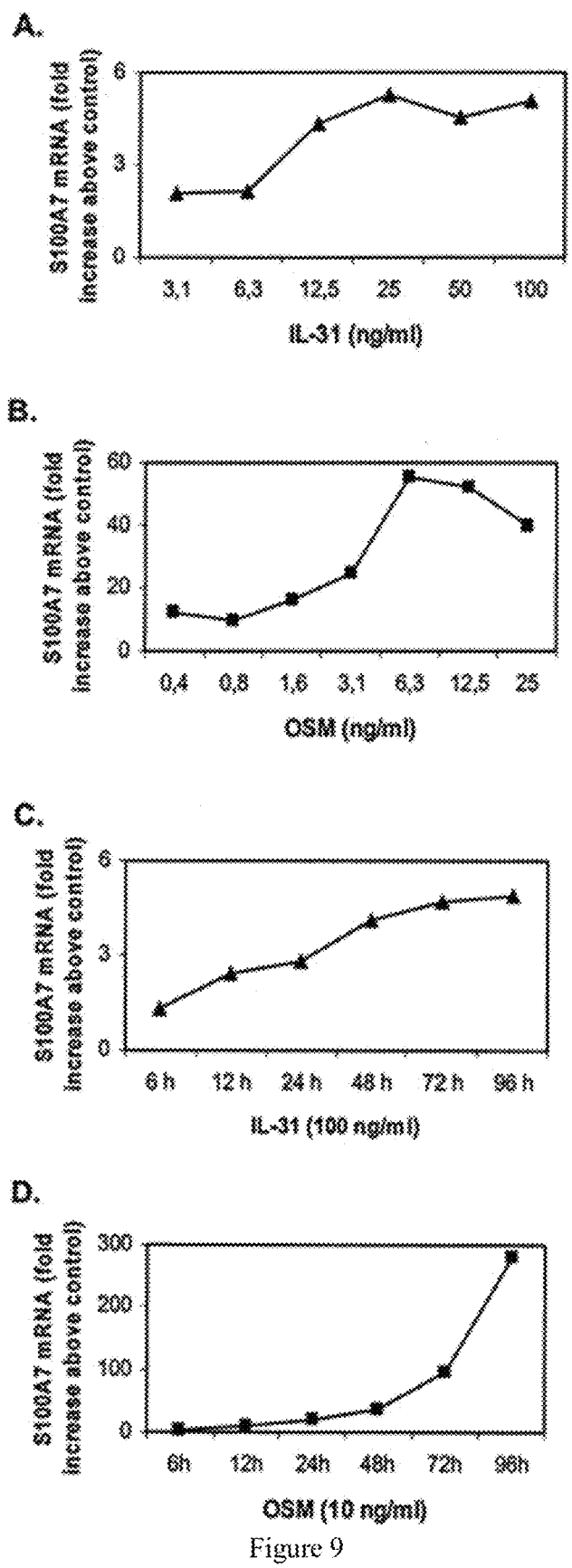

FIG. 9 shows the effect of IL-31 and OSM on S100A7 mRNA expression.

NHEK were cultured with or without 3.1, 6.3, 12.5, 25, 50 or 100 ng/ml of IL-31 (A) or with or without 0.4, 0.8, 1.6, 3.1, 6.3, 12.5 or 25 ng/ml of OSM (B) for 48 h. Kinetic study of S100A7 mRNA expression in the absence or presence of 100 ng/ml of IL-31 (C) or 10 ng/ml of OSM (D). Total RNA was extracted, reverse transcribed, and S100A7 and HMBS mRNA relative expression was quantified by real time PCR. HMBS was used as a housekeeping gene to normalize gene expression as detailed in Materials and Methods. Results, expressed as the relative expression of stimulated cells over control cells, are representative of 2 independent experiments.

Figure 10:
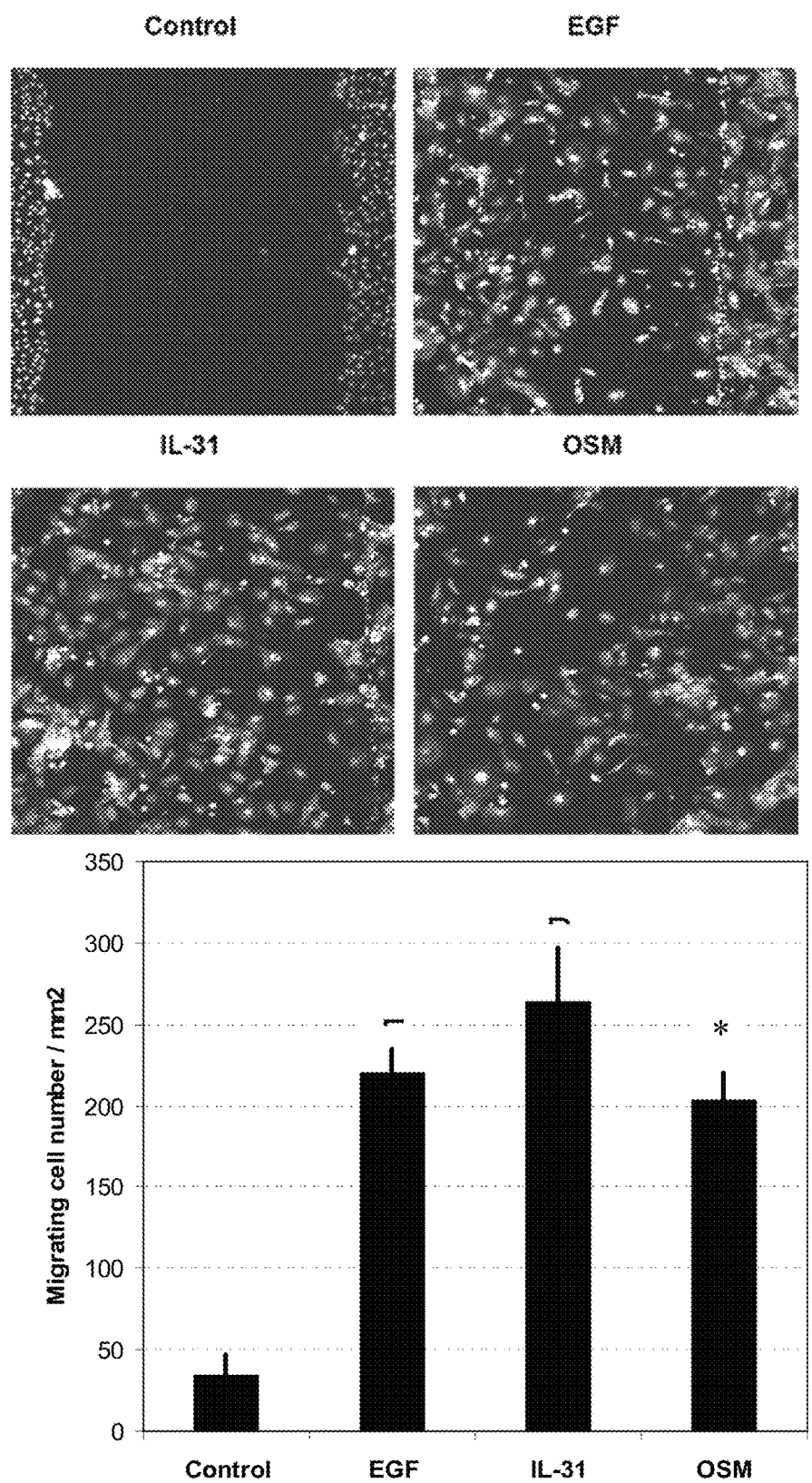

FIG. 10 shows the effect of IL-31 and OSM on keratinocyte migration.

In vitro wounds were introduced in mitomycin-treated confluent NHEK culture and the keratinocytes were cultured for 48 h with or without 100 ng/ml of IL-31, or 10 ng/ml of EGF or OSM. Cell migration to the cell free area was assessed as described in Materials and Methods. Each bar represents the mean±SEM of migrating keratinocytes counted in 4 non-overlapping fields. One experiment representative of 2. * p<0.001 compared with respective control without cytokine, based on Student's t test.

Figure 11:
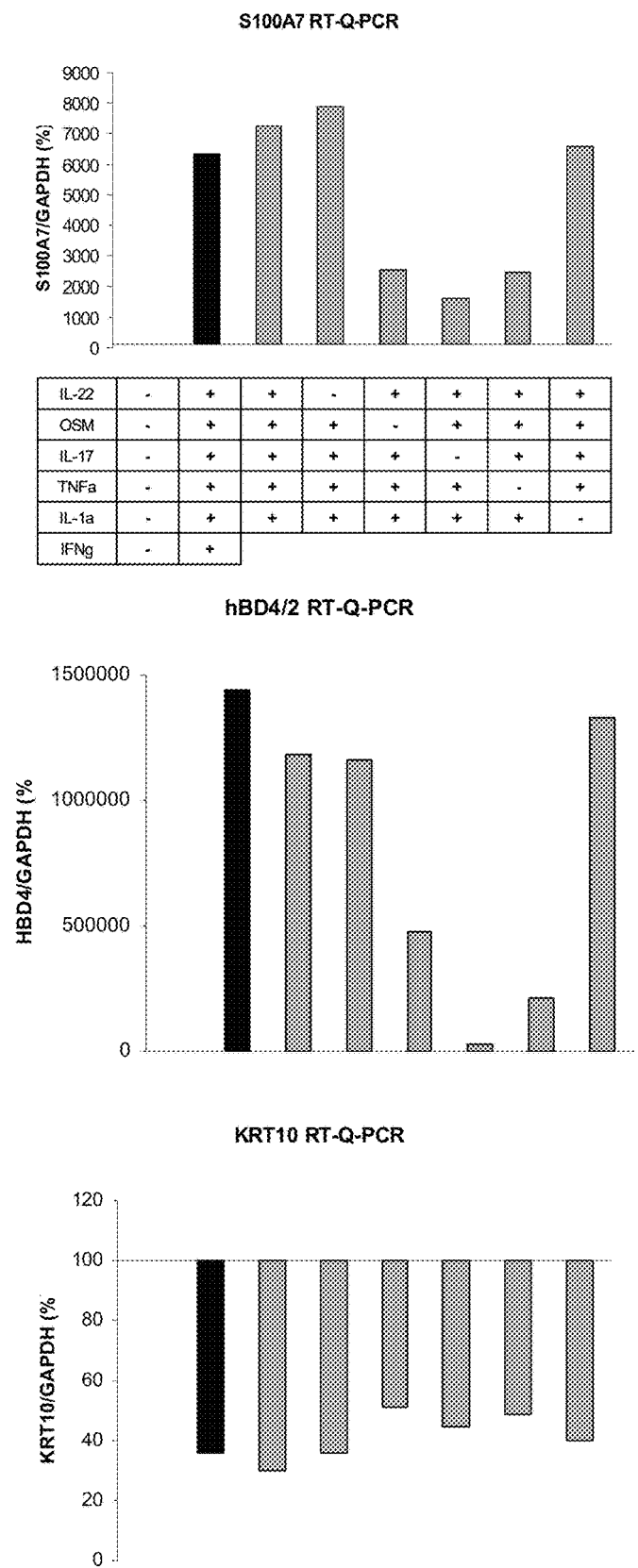

FIG. 11 shows the effect of several cocktails of cytokines on S100A7, hBD4/2, and KRT10 mRNA expression.

Confluent normal human keratinocytes (NHEK) were treated for 24 hrs with the indicated mixed cytokine (each cytokine at 1 ng/ml final concentration). Total RNA was extracted, reverse-transcribed and the expression of the selected genes was analyzed by real-time PCR.

Figure 12:
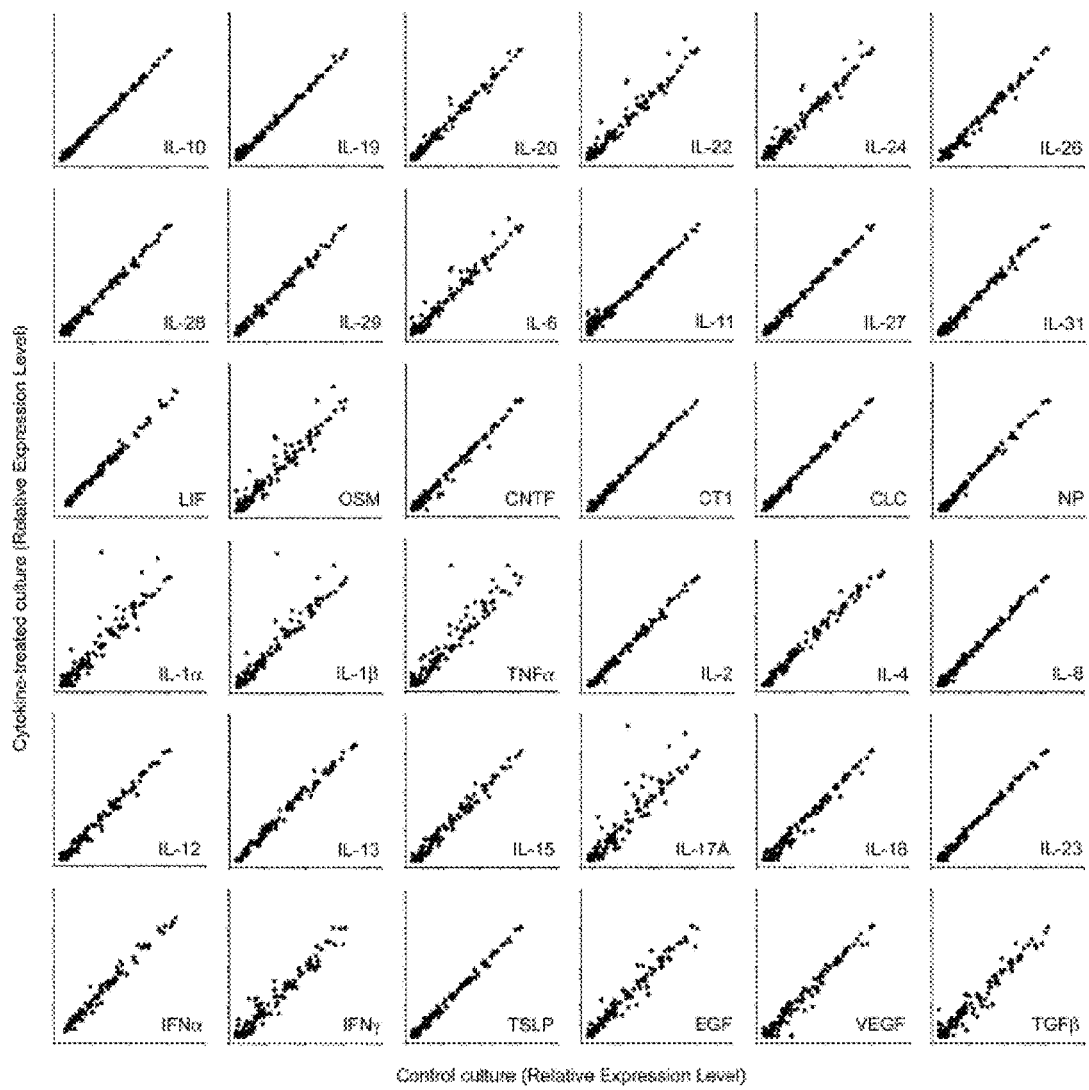

FIG. 12: Cytokine-stimulated keratinocyte transcriptional profile. Comparison of the effects of 36 cytokines on the overall expression of a panel of 154 genes of potential interest for skin physiology was performed using home-made cDNA macroarrays analysis. NHEK were cultured with 10 ng/ml of each cytokine for 24 h. Total RNA was extracted and conventional 33P-cDNA target synthesis and hybridization were performed. For each cytokine, the relative expression of each gene in the stimulated culture is plotted versus that of the control culture.

Figure 13:
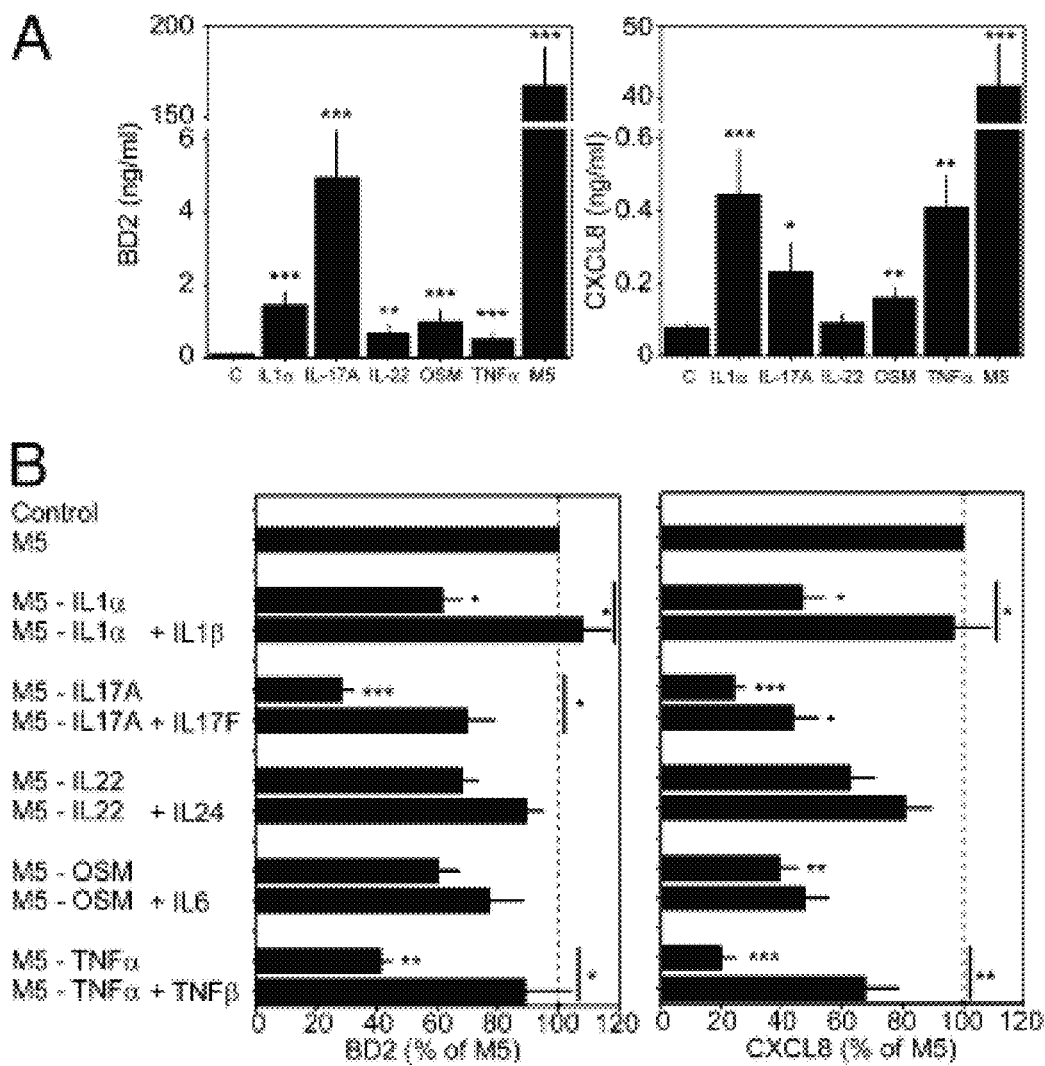

FIG. 13: BD2 and CXCL8 production by keratinocyte after stimulation by IL-1α, IL-17A, IL-22, OSM and TNFα or by cytokines of the same family. NHEK were cultured with (A) 10 ng/ml of IL-1α, IL-17A, IL-22, OSM and TNFα alone or in combination (M5) or (B) after substitution by cytokines of the same family. After 96 h, BD2 and CXCL8 secreted in culture supernatants were measured by ELISA (7 independent experiments). Statistical comparisons were performed using either Mann-Whitney or Kruskal-Wallis ANOVA and Dunn's test for multiple comparisons (* p<0.05,  p<0.01, * p<0.001).

Figure 14:
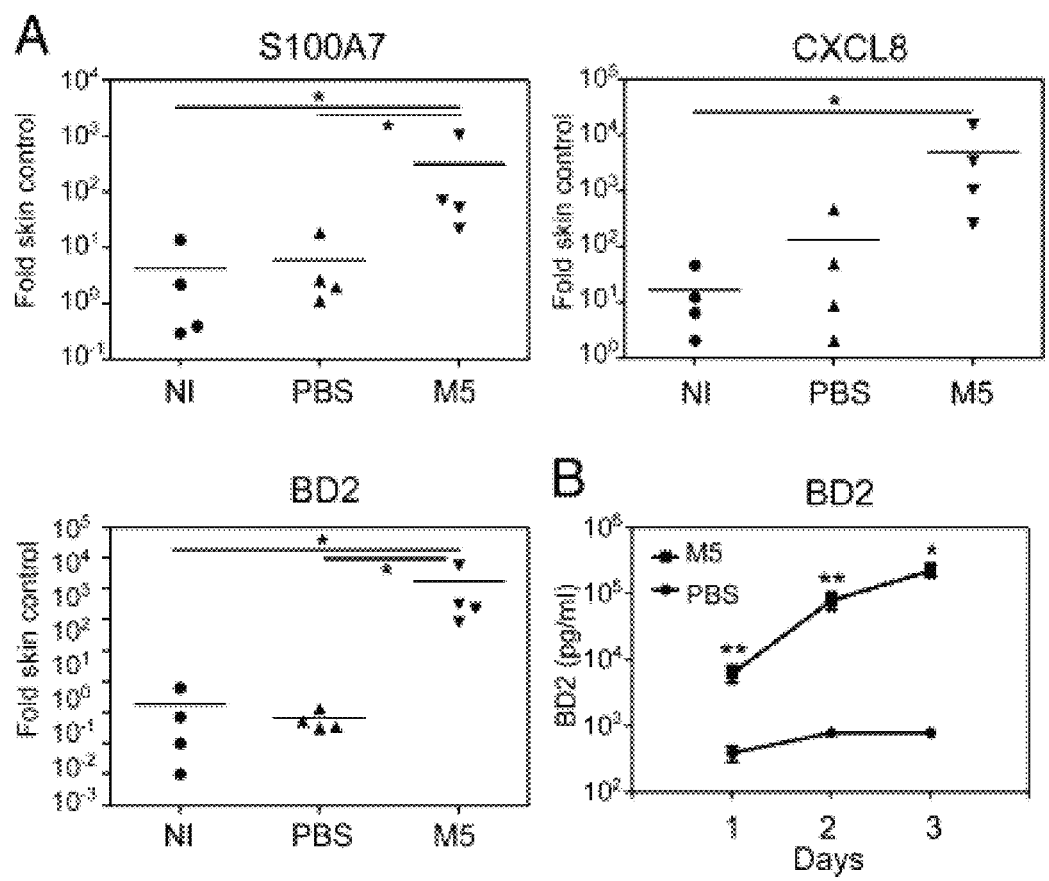

FIG. 14: Expression of antimicrobial peptides and chemokines by human skin explants after cytokine injections. Human skin explants were injected with 10 ng of IL-1α, IL-17A, IL-22, OSM and TNFα (M5), with PBS (PBS) or non-injected (NI) and cultured for 24 h, 48 h and 72 h (4 independent experiments). (A) After 24 h treatment, quantitative RT-PCR analysis was carried out for S100A7, CXCL8 and BD2, normalized using housekeeping genes and expressed as the fold increase above normal skin. (B) BD2 secreted in culture supernatants was measured by ELISA. Statistical comparisons were performed using Mann-Whitney test (* p<0.05, ** p<0.01).

Figure 15:
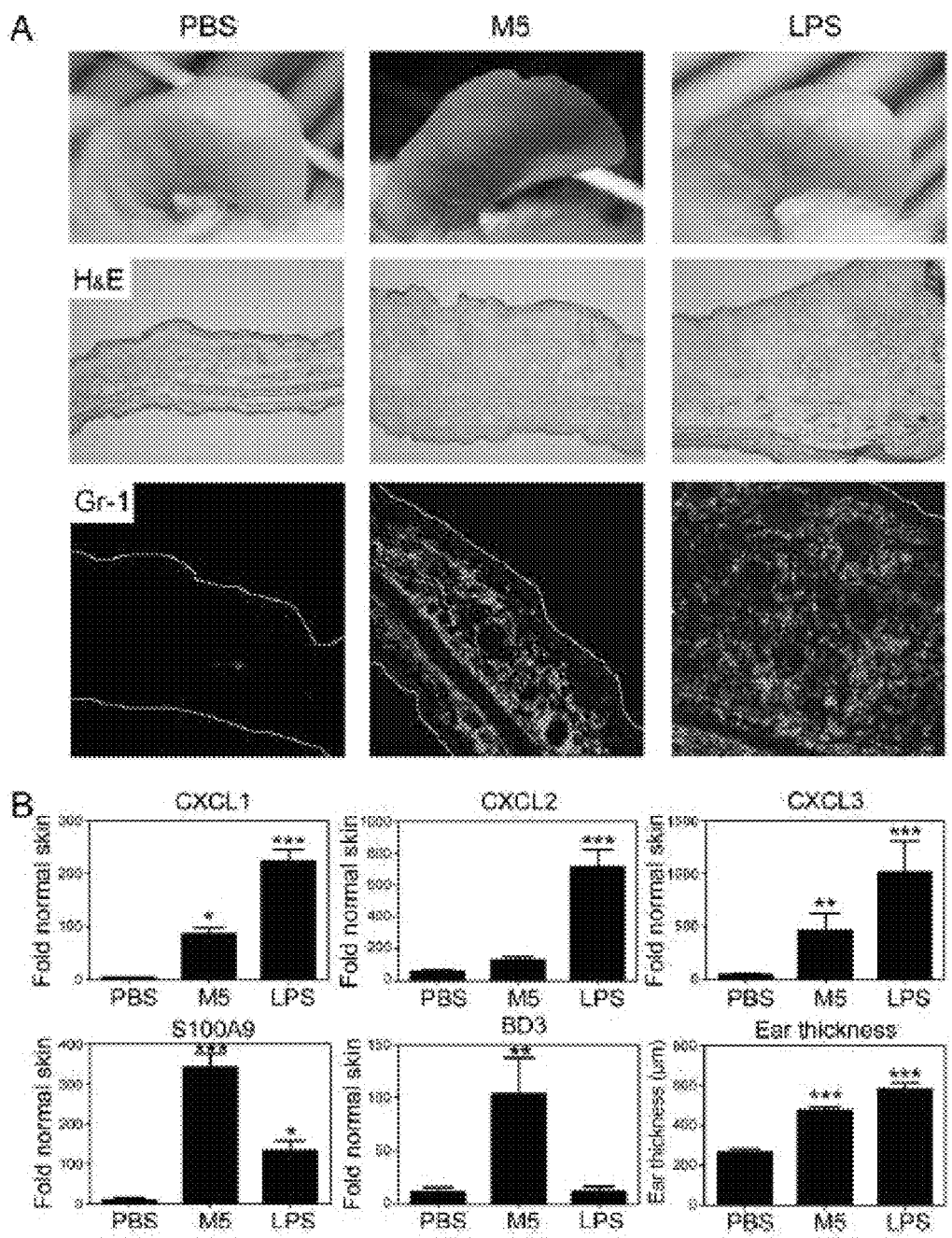

FIG. 15: Cytokine-induced skin ear inflammation. Ears from outbred OF1 mice (n=3 for each group) were injected intradermally with 250 ng of IL-1α, IL-17A, IL-22, OSM and TNFα, with PBS or with 10 µg of LPS. (A) On day 2, ears were collected for staining with H&E and immunodetection of neutrophils using anti-Gr-1 mAb. (B) On day 1, quantitative RT-PCR analysis was carried out on RNA isolated from treated ears, normalized using housekeeping genes and expressed as the fold increase above untreated skin. Ear thickness at day 2 was measured. Statistical comparisons were performed using Kruskal-Wallis ANOVA and Dunn's test for multiple comparisons (* p<0.05,  p<0.01, * p<0.001).

Figure 16:
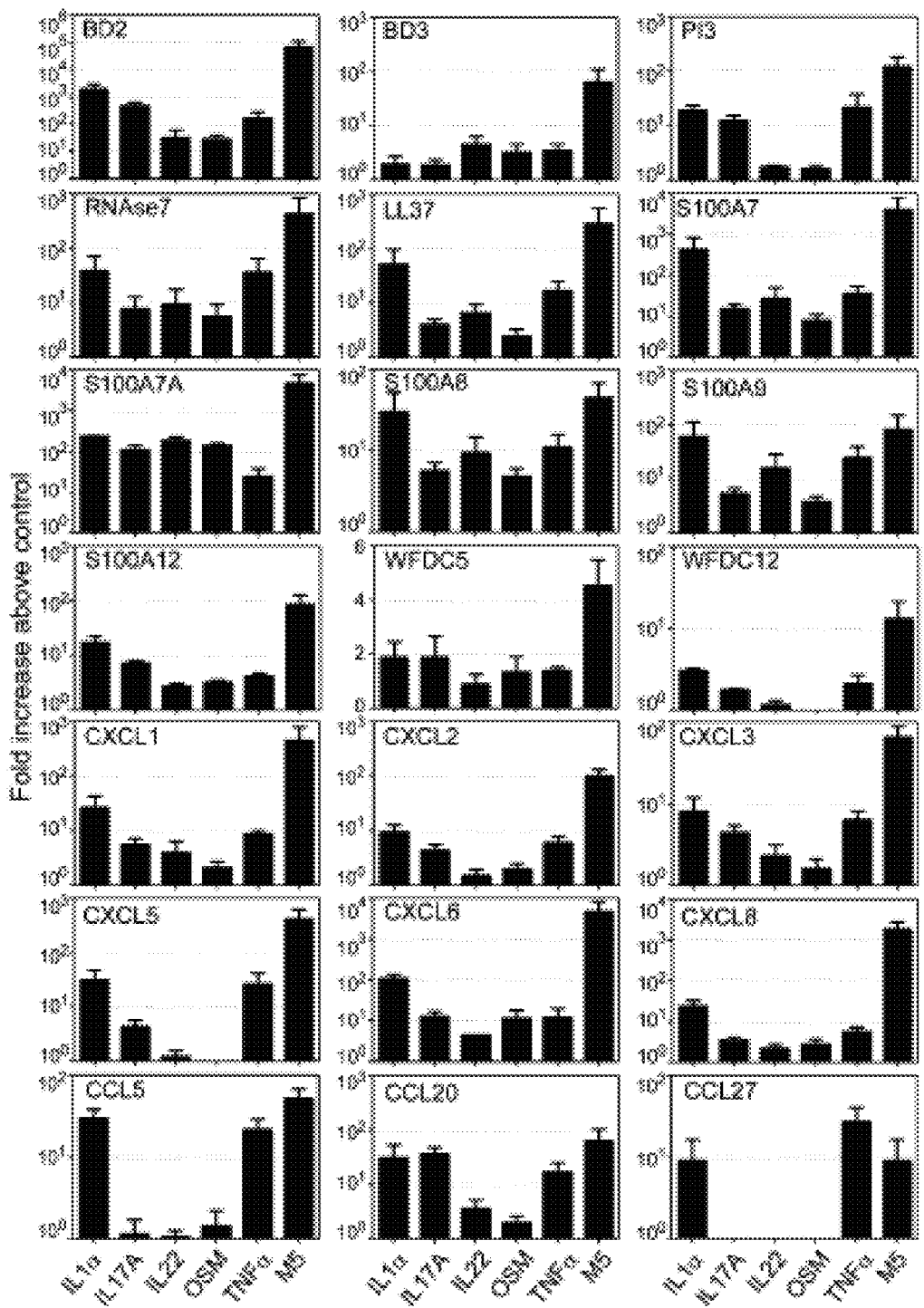

FIG. 16: Antimicrobial peptides and chemokines gene expression by cytokine-stimulated keratinocytes. NHEK were cultured in the presence or absence of 10 ng/ml IL-1α, IL-17A, IL-22, OSM and TNFα alone or in combination (M5) for 24 h. Quantitative RT-PCR analysis was carried out on total RNA from 6 independent NHEK cultures. mRNA expression levels are normalized using housekeeping genes and expressed as the fold increase above unstimulated cultures.

Figure 17:
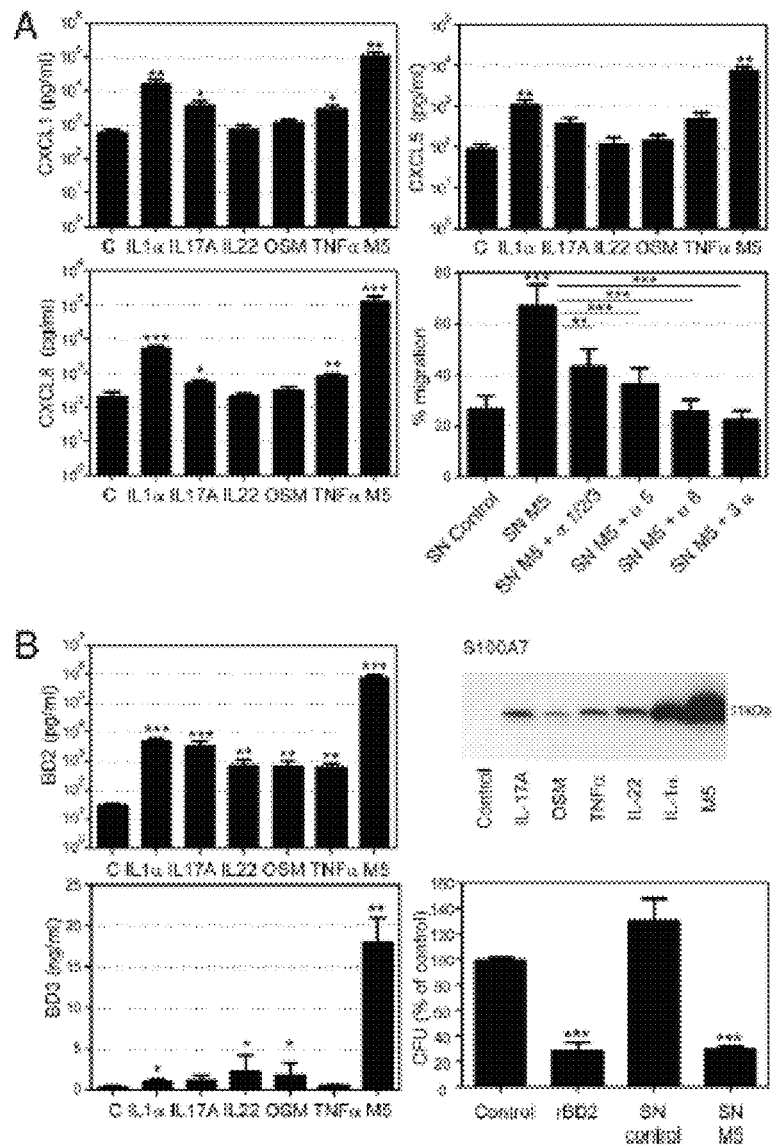

FIG. 17: Neutrophil chemotactic activity and antimicrobial activity of cytokine-stimulated keratinocytes. (A) Keratinocytes were treated with 10 ng/ml of cytokines alone or in combination (M5). After 96 h, chemokines secreted in culture supernatants were measured by ELISA and culture supernatants were tested for chemotactic activity on human neutrophils, with or without blocking mAbs against CXCL1/2/3 (α1/2/3), CXCL5 (α5), CXCL8 (α8) or the combination of these three mAbs (3α). (B) Keratinocytes were treated with 10 ng/ml of cytokines alone or in combination (M5). After 96 h, BD2 and BD3 secreted in culture supernatants were measured by ELISA and S100A7 in cell lysates detected by Western blot. Antimicrobial activity of the keratinocyte culture supernatants (control or M5) against *E. coli* was analyzed using a CFU assay. Five ng/ml of recombinant BD2 was used as positive control. Statistical comparisons were performed using either Mann-Whitney or Kruskal-Wallis ANOVA and Dunn's test for multiple comparisons (* p<0.05,  p<0.01, * p<0.001).

Figure 18:
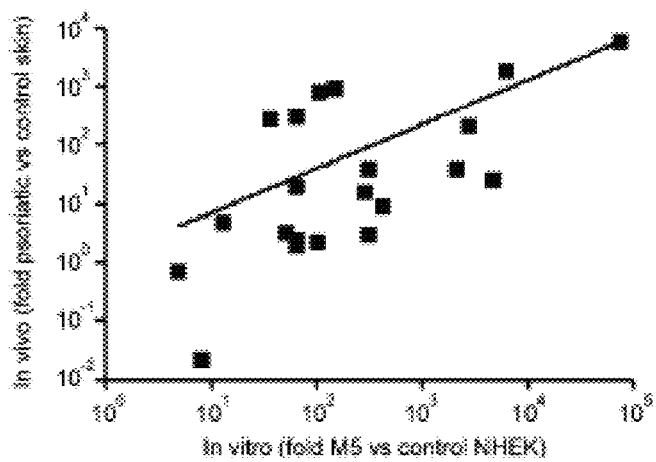

FIG. 18: Transcriptional profiles of in vitro inflammatory keratinocytes and psoriatic skin. Quantitative RT-PCR analysis was carried out on NHEK cultures stimulated or not with M5, control skin and psoriatic skin. The ratio of relative expression of M5 versus unstimulated cultures (n=6) and the ratio of relative expression of psoriatic versus normal skin (n=8) were compared. Comparison study was performed using the Spearman rank correlation test (r=0.58, p=0.0063).

Figure 19:
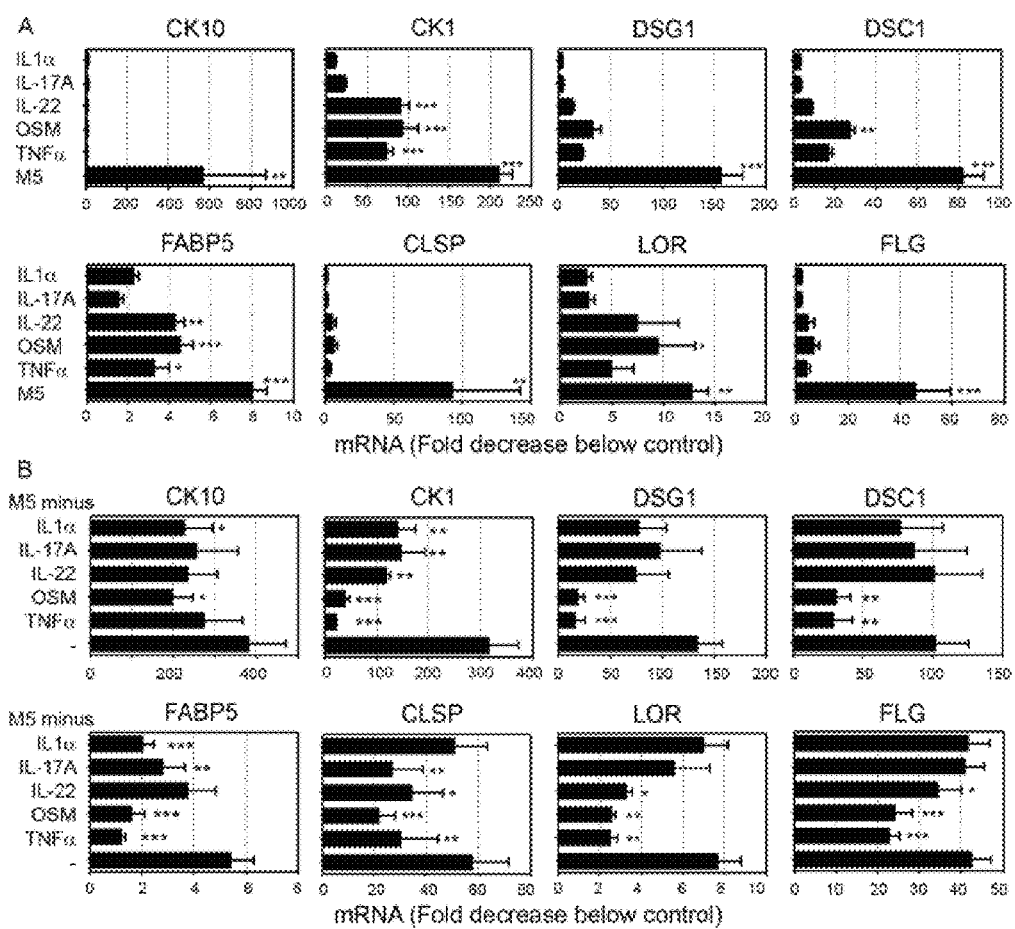

FIG. 19: Synergistic activity of proinflammatory cytokines on inhibition of KDM expression by NHEK. NHEK were cultured in the presence or absence of 10 ng/ml of IL-1α, IL-17A, IL-22, OSM and TNFα alone or in combination for 24 h. Quantitative RT-PCR analysis was carried out on total RNA from 4 independent NHEK cultures. mRNA expression levels for cytokeratin 10 (CK10), cytokeratin 1 (CK1), desmoglein 1 (DSG1), desmocollin 1 (DSC1), fatty acid binding protein 5 (FABP5), calmodulin-like skin protein (CLSP), loricrin (LOR) and filaggrin (FLG) were normalized using GAPDH housekeeping gene and expressed as the fold decrease under unstimulated cultures.

(A) Comparison of the activity of IL-1α, IL-17A, IL-22, OSM and TNFα alone or in combination (M5) on expression of keratinocyte differentiation markers.

(B) Comparison of the activity of mix of 4 cytokines versus mix of 5 cytokines (M5) on expression of keratinocyte differentiation markers.

All data are represented as mean and SEM of 4 independent experiments. One-way ANOVA with a Dunnett post-test were used for statistical evaluation and p values were as follows: *p<0.05, p<0.01, *p<0.001.

Figure 20:
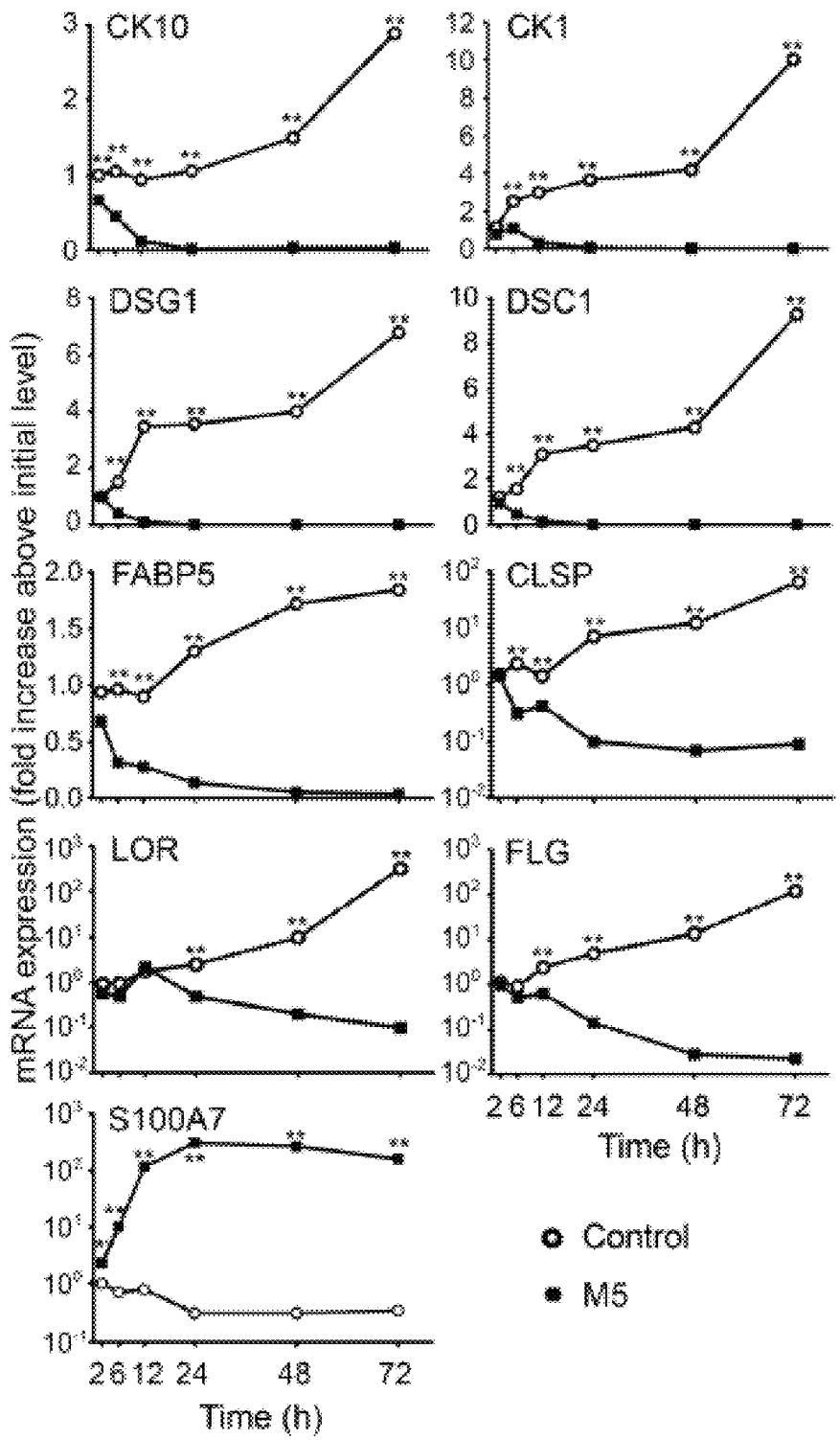

FIG. 20: Sustained inhibition of differentiation in NHEK cultured with combination of IL-1α, IL-17A, IL-22, OSM, TNFα. NHEK were cultured in the presence or absence of 10 ng/ml IL-1α, IL-17A, IL-22, OSM and TNFα in combination (M5) for 2 h to 72 h. Quantitative RT-PCR analysis was carried out and mRNA expression levels for cytokeratin 10 (CK10), cytokeratin 1 (CK1), desmoglein 1 (DSG1), desmocollin 1 (DSC1), fatty acid binding protein 5 (FABP5), calmodulin-like skin protein (CLSP), loricrin (LOR), filaggrin (FLG) and S100A7 were normalized using GAPDH housekeeping gene and expressed as the fold increase above initial unstimulated control. Results are from one experiment representative of two. A Mann-Whitney test was used for statistical evaluation and p values were as follows: *p<0.05, **p<0.01.

Figure 21:
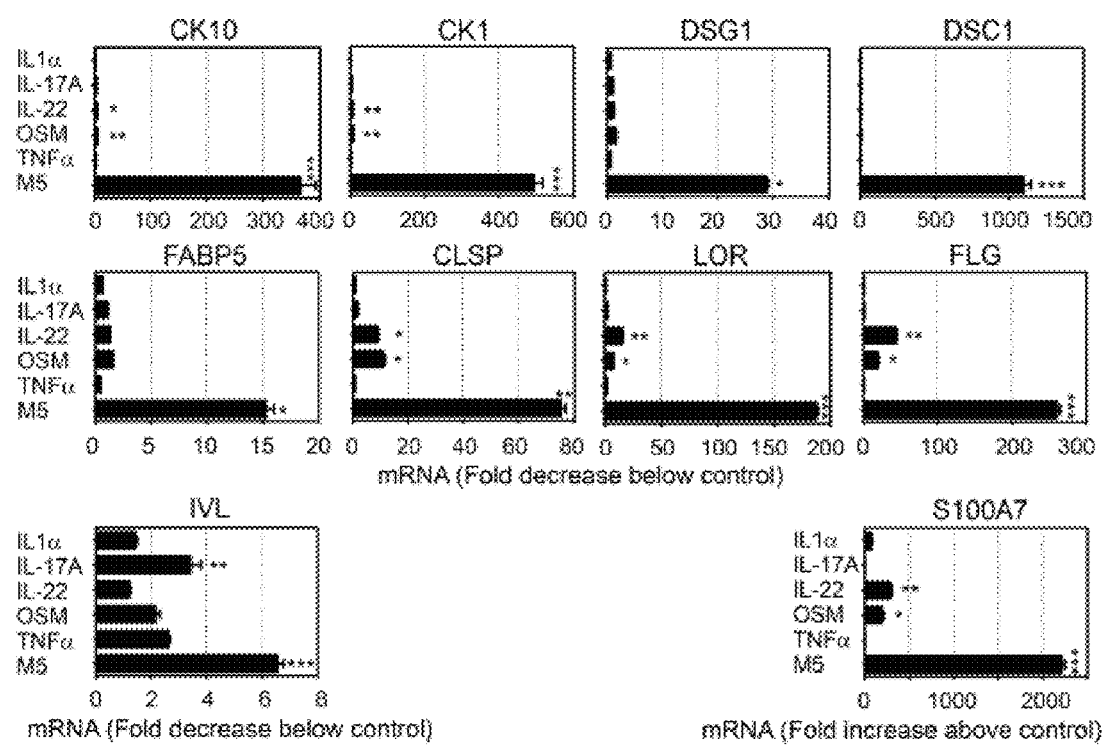

FIG. 21: Synergistic activity of proinflammatory cytokines on inhibition of KDM expression by Reconstituted Human Epidermis.

RHE have been cultured for 10 days at the air-water interface using an appropriate differentiation medium and then with or without recombinant IL-1α, IL-17A, IL-22, OSM or TNFα alone or in combination during 24 h for mRNA quantification. Quantitative RT-PCR analysis was carried out and expression levels for KDM were normalized using GAPDH housekeeping gene and expressed as the fold to unstimulated control cultures. Data are mean and SEM of one experiment representative of two. One-way ANOVA with a Dunnett post-test were used for statistical evaluation and p values were as follows: *p<0.05, p<0.01, *p<0.001.

Figure 22:
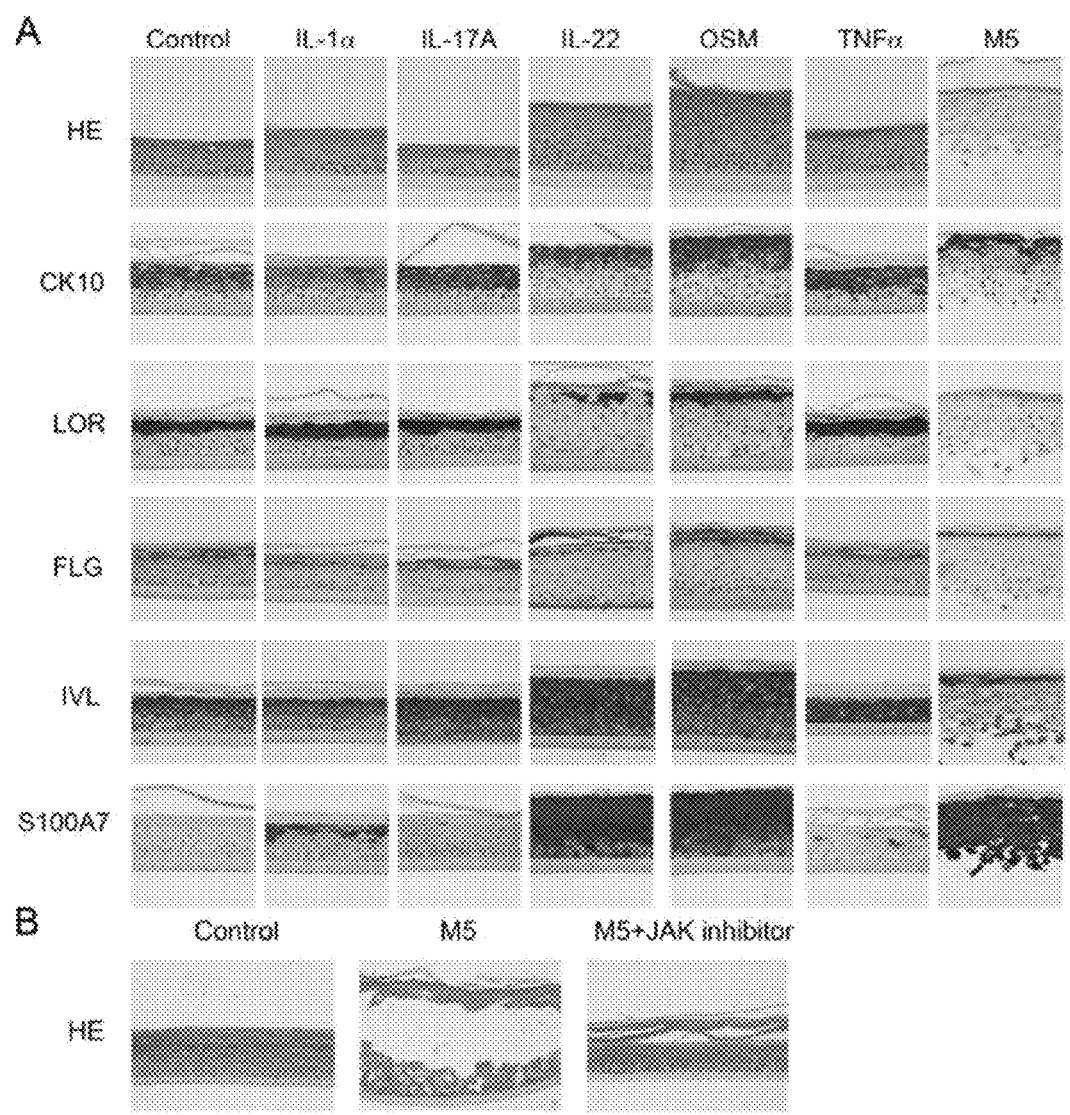

FIG. 22: Activities of proinflammatory cytokines on the differentiation of Reconstituted Human Epidermis.

(A) RHE have been cultured for 10 days at the air-water interface using an appropriate differentiation medium and then with or without recombinant IL-1α, IL-17A, IL-22, OSM or TNFα alone or in combination during 72 h for immunohistological analysis. RHE were fixed, embedded in paraffin and 4 μm vertical sections were stained with Hematoxylin and Eosin (HE) or with anti-CK10, anti-LOR, anti-FLG, anti-IVL or anti-S100A7 mAbs. Results are from one experiment representative of two.

(B) RHE have been cultured for 10 days at the air-water interface using an appropriate differentiation medium and then with or without recombinant IL-1α, IL-17A, IL-22, OSM and TNFα (3 ng/ml), with or without JAKs inhibitor (10 μM) during 72 h. RHE were fixed, embedded in paraffin and 4 μm vertical sections were stained with Hematoxylin and Eosin. Results are from one experiment representative of three.

Figure 23:
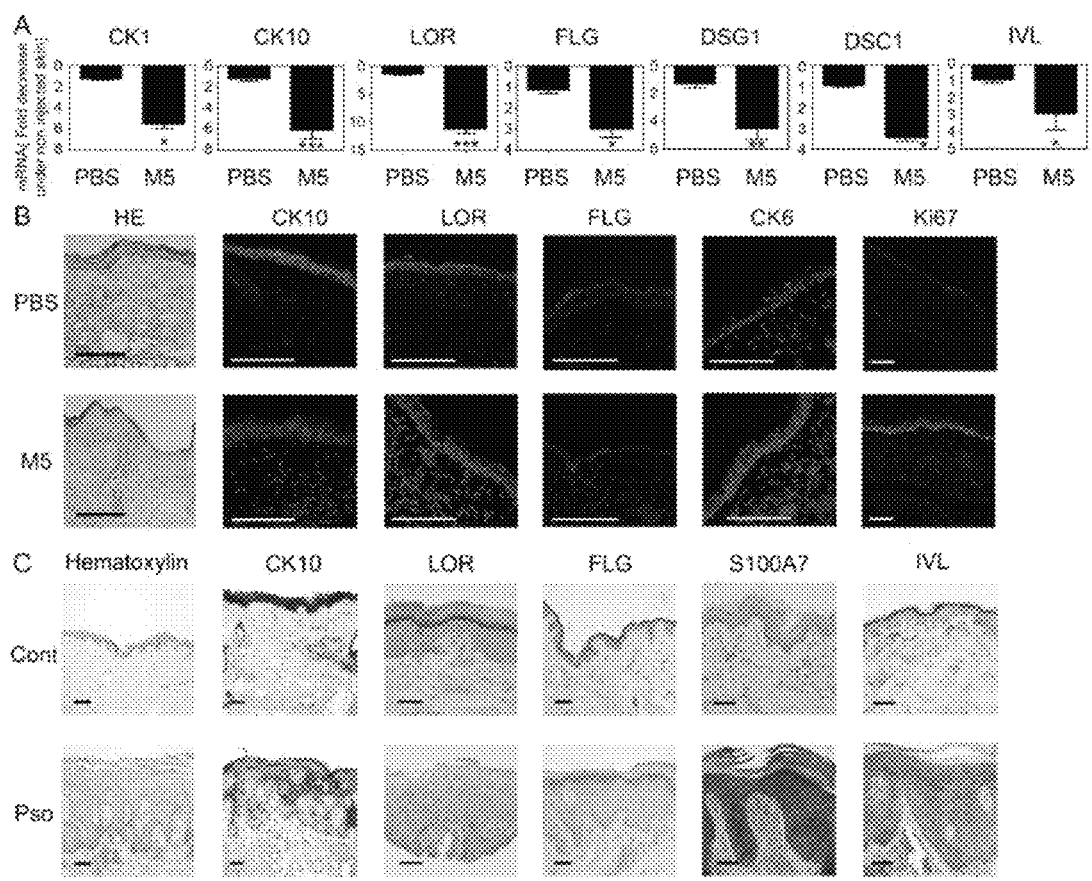

FIG. 23: Inhibition of KDM expression in vivo (A) Ears from C57Bl/6 mice were injected intradermally with 250 ng of IL-1α, IL-17A, IL-22, OSM and TNFα (M5) or with Phosphate Buffered Saline (PBS). At 24 h quantitative RT-PCR analysis was carried out on total RNA and expression levels for cytokeratin 1 (CK1), cytokeratin 10 (CK10), loricrin (LOR), filaggrin (FLG), desmoglein 1 (DSG1), desmocollin 1 (DSC1) and involucrin (IVL) were normalized using GAPDH housekeeping gene and expressed as the fold decrease under non injected skin. Data are represented as mean and SEM of 3 independent experiments. *p<0.05, p<0.01, *p<0.001

(B) On day 2, the ears were collected for staining with Hematoxylin and Eosin (HE) and immunodetection of cytokeratin 10, loricrin, filaggrin, cytokeratin 6 and Ki-67. Scale bar 100 μm. Results are from one experiment representative of three.

(C) Skin biopsies from normal control skin (Cont) or lesional psoriatic skin (Pso) were collected. Skin sections were stained with Hematoxylin and immunodetection of cytokeratin 10, loricrin, filaggrin, involucrin and S100A7 was performed. Scale bar 100 µm. Results are from one experiment representative of three.

DETAILED DESCRIPTION OF THE INVENTION

The inventors found that several cytokines, in particular OSM and IL-31, can enhance the migration of keratinocytes. Interestingly, these two cytokines bind to different heteromeric receptors, that both comprise OSMRβ as a subunit. The inventors have shown that normal human epidermal keratinocytes express gp130, GPL and OSMRβ.

As disclosed in the experimental examples below, OSM recruits the STAT3 signaling pathways, as well as the MAP kinase pathways in human epidermal keratinocytes. OSM up-regulates the expression of pro-inflammatory genes in these cells, including chemokines, defensin and the psoriasin. OSM also increases the thickness of reconstituted human epidermis and down-regulates a set of differentiation antigens. Interestingly, other cytokines, especially IL-17 and TNFα, act synergistically with OSM and potentiate its effects.

Experiments conducted by the inventors also revealed that IL-31 can mediate keratinocyte migration. The inventors however observed, in glioblastoma and melanoma tumor cells, that the action of IL-31 depends on the type of GPL subunit involved with OSMRβ in the formation of the heteromeric receptor. In particular, they noticed that a short form of GPL receptor exerts a profound inhibitory effect on the signaling of IL-31 and behaves as a dominant negative receptor.

The inventors also demonstrated that the combination of IL-17A, IL-22, IL-1α, OSM and TNFα synergistically increased production of CXCL8 and β-Defensin2 (BD2). These five cytokines synergistically increase chemokine and antimicrobial-peptide expression, recapitulating some features of psoriasis. Production of CXCL1, CXCL5, and CXCL8 by keratinocytes stimulated in the presence of this cytokine combination was associated with increased neutrophil chemotactic activity. Similarly, high production of β-Defensin2, β-Defensin3, and S100A7 was associated with an increased antimicrobial activity. As shown in example 14 below, all of these 5 cytokines decreased keratinocyte differentiation markers although IL-22, OSM were the most powerful, and that the five cytokines strongly synergize the effects. IL-22 and OSM more specifically drive epidermal hyperplasia and differentiation loss while IL-1α, IL-17A and TNFα were more involved in the activation of innate immunity.

Provided herein is a method for improving epidermal repair and/or cutaneous innate immunity, comprising administering IL-1α, IL-17 and TNFα to a patient in need thereof. According to a preferred embodiment, oncostatin M (OSM) and/or IL-22 are also administered to the patient, either simultaneously or sequentially. The compositions can be administered in a composition, for example in a composition formulated for topical administration. In the present text, IL-17 designates IL-17A, IL-17B or a mixture thereof. According to a preferred embodiment IL-17 is IL-17A.

The method according to the present invention is useful, inter alia, for promoting epidermal healing, for promoting keratinocyte migration for increasing epidermal thickness, for preventing and/or attenuating chaps on hands, lips, face or body, for preventing and/or attenuating stretch marks, for improving the aspect and comfort of scars and for improving the aspect and comfort of epidermal wounds during their cicatrisation.

The present invention also pertains to a method for increasing the expression of anti-microbial peptides by keratinocytes, comprising contacting said keratinocytes with a composition comprising IL-1α, IL-17, TNFα, IL-22 and OSM.

Another aspect of the present invention is a composition comprising IL-1α, IL-17 and TNFα. Advantageously, the composition further comprises IL-22 and/or OSM. According to a preferred embodiment, this composition is a cosmetic and/or dermatological composition.

Compositions obtained according to the invention can be used for promoting keratinocyte migration, or for promoting epidermal healing. These compositions will advantageously be used for stimulating centripetal migration of keratinocytes in case of large wounds. They can also be used for preventing, attenuating or treating bullous epidermolysis. Indeed, depending on its origin and stage, bullous epidermolysis can be treated either by administering molecules enhancing keratinocyte migration, or, to the contrary, anti-inflammatory molecules. The physician will know, depending on the context, when a treatment with OSM, IL-31 and/or their agonists and potentiators, can be beneficial for a patient suffering from bullous epidermolysis.

The compositions according to the invention can also be used for increasing epidermal thickness, either in vivo, for example by topical administration, or in vitro, to increase the quality and/or quantity of (human) reconstituted epidermis, for example to accelerate the production of epithelial layers for patients in need of a graft.

According to specific embodiments of the present invention, a mix of cytokines as described above is used for the preparation of a composition for preventing and/or attenuating chaps on hands, lips, face or body, or for preventing and/or attenuating stretch marks. Other applications of the compositions obtained according to the invention are the improvement of the aspect and comfort of scars, and/or the improvement of the aspect and comfort of epidermal wounds during their healing. According to this aspect of the invention, the wounds can be of any origin. They include those resulting from trauma such as cuts, burns, abrasions and the like, those resulting from surgical procedures such as surgical incisions and skin grafting, as well as those resulting from disorders and diseases like acne, atopic dermatitis, eczema, professional dermatitis, seborrheic dermatitis, rosacea, erythema, eschar, diabetes (feet), keratosis, squama, ulcers, ichtyosis, bullous epidermolysis, malum perforan pedis, wart, leprae infection, etc. Of course, in the case of wounds resulting from inflammatory diseases, or from diseases related to keratinocyte hyperproliferation, the physician will control that the disease is treated before the composition according to the invention is administered.

The compositions prepared according to the invention are preferably formulated for topical administration. They can for example be in the form of a cream, lotion, ointment, or dressing.

Particular cosmetic and/or dermatological compositions according to the invention comprise IL-1α, IL17A, OSM, IL-22 and TNFα.

The invention also pertains to the use of at least IL-1α, IL17A and TNFα, for the preparation of dermatological and/or cosmetic compositions. These cytokines can be either mixed in the same composition, or provided in a kit of parts.

In the compositions according to the invention comprising OSM, OSM is preferably in a concentration of 0.1 to 100 ng/ml, more preferably from 1 to 20 ng/ml. Its concentration can be lowered in the presence of IL-17 and/or TNFα, down to 0.01 ng/ml. In such complex compositions, the concentrations of OSM and/or IL-17 and/or TNFα are preferably from 0.01 ng/ml to 10 ng/ml, more preferably from 0.1 to 2 ng/ml.

The invention is further illustrated by the following examples:

EXAMPLES

Example 1: Material and Methods

Cell Cultures, Cytokines and Reagents

NHEK were obtained from surgical samples of healthy breast skin. The use of these samples for research studies was approved by the Ethical Committee of the Poitiers Hospital. Skin samples were incubated overnight at 4° C. in a dispase solution (25 U/ml; Invitrogen Life Technologies, Cergy Pontoise, France). Epidermal sheets were removed from dermis and NHEK were dissociated by trypsin digestion (trypsin-EDTA, Invitrogen) for 15 min at 37° C. Cells were cultured in Serum-Free Keratinocyte Medium (Keratinocyte SFM) supplemented with bovine pituitary extract (25 µg/ml) and recombinant epidermal growth factor (0.25 ng/ml; all purchased from Invitrogen). NHEK were starved for 48 h in Keratinocyte SFM without addition of growth factors before stimulation.

Human recombinant OSM, IL-5, IL-6, soluble IL-6R were purchased from R&D Systems (Oxon, UK). The IgG1 isotype control (MC192), anti-gp130 (AN-HH1), anti-OSMR antibody (AN-A2) and anti-LIFR (AN-E1) were produced in the laboratory. Antibodies raised against phospho-STAT3, phospho-MAPK, MAPK were bought from Upstate Biotechnology (Lake Placid, N.Y.). Anti-STAT3, anti-S100A8 and anti-S100A9 antibodies were from Santa Cruz Biotechnology (Santa Cruz, Calif., USA). Anti-S100A7 antibody was purchased from Imgenex (San Diego, Calif., USA). Goat anti-mouse and anti-rabbit peroxidase labelled immunoglobulins were from Cliniscienes (Montrouge, France), and rabbit anti-goat peroxidase-conjugated antibody was from Sigma (Amersham Biosciences).

RT-PCR and RT-Real Time PCR Analysis

Total cellular RNA was isolated using Trizol reagent (Invitrogen) and treated with DNase I (0.05 U/µl; Clontech, Palo Alto, Calif., USA). cDNAs were synthesised from 2 µg of total RNA by random hexamer primers using MMLV reverse transcriptase (Promega, Madison, Wis.). Reverse transcription products were subsequently amplified by 25 cycles of PCR using primers for OSMR (forward 5'-CCTGCCTACCTGAAAACCAG-3' (SEQ ID No: 1) and reverse 5'-ACATTGGTGCCTTCTTCCAC-3' (SEQ ID No: 2)), gp130 (forward 5'-GGGCAATATGACTCTTTGAAGG-3' (SEQ ID No: 3) and reverse 5'-TTCCTGTTGATGTTCAGAATGG-3' (SEQ ID No: 4)), LIFR (forward 5'-CAGTACAAGAGCAGCGGAAT-3' (SEQ ID No: 5) and reverse 5'-CCAGTCCATAAGGCATGGTT-3' (SEQ ID No: 6)) and GAPDH (forward 5'-ACCACAGTCCATGCCATCAC-3' (SEQ ID No: 7) and reverse TCCACCACCCTGTTGCTGTA (SEQ ID No: 8)). Amplified products were analysed by 2% agarose gel electrophoresis.

Quantitative real time PCR was carried out using the LightCycler-FastStart DNA Master$^{PLUS}$ SYBR Green I kit (Roche, Mannheim, Germany). The reaction components were 1× FastStart DNA Master$^{PLUS}$ SYBR Green I and 0.5 µM of forward and reverse primers for S100A7 (forward 5'-GCATGATCGACATGTTTCACAAATACAC-3' (SEQ ID No: 9) and reverse 5'-TGGTAGTCTGTGGCTATGTCTCCC-3' (SEQ ID No: 10)), S100A8 (Pattyn, Speleman et al. 2003), S100A9 (forward 5'-GCTCCTCGGCTTTGACAGAGTGCAAG-3' (SEQ ID No: 11) and reverse 5'-GCATTTGTGTCCAGGTCCTCCATGATGTGT-3' (SEQ ID No: 12)), hBD2/4 (forward 5'-GCCATCAGCCATGAGGGTCTTG-3' (SEQ ID No: 13) and reverse 5'-AATCCGCATCAGCCACAGCAG-3' (SEQ ID No: 14)), KRT10 (forward 5'-GCCCGACGGTAGAGTTCTTT-3' (SEQ ID No: 15) and reverse 5'-CAGAAACCACAAAACACCTTG-3' (SEQ ID No: 16)), and hydroxymethyl-bilane synthase (HMBS) as a housekeeping gene (Vandesompele, De Preter et al. 2002). After cDNA fluorescent quantification using propidium iodide, 250 ng, 25 ng and 2.5 ng of cDNA were added as PCR template in the LightCycler glass capillaries. The cycling conditions comprised a 10 min polymerase activation at 95° C. and 50 cycles at 95° C. for 10 s, 64° C. for 5 s and 72° C. for 18 s with a single fluorescence measurement. Melting curve analysis, obtained by increasing temperature from 60° C. to 95° C. with a heating rate of 0.1° C. per second and a continuous fluorescence measurement, revealed a single narrow peak of suspected fusion temperature. A mathematical model was used to determine the relative quantification of target genes compared to HMBS reference gene (Pfaffl 2001).

Gene Expression Profiling Using cDNA Macroarrays

Total RNA was isolated as described for PCR studies. DNase treatment, polyA$^+$ RNA enrichment, $^{33}$P-labelled cDNA probe synthesis, purification and hybridization to custom Atlas array membranes (Bernard, Pedretti et al. 2002) were performed according to Clontech's recommendations (Clontech, Palo Alto, USA). Membranes were exposed for 5 days to a Molecular Dynamics Storm storage screen and scanned using a phosphorimager scanner (Molecular Dynamics Storm analyser, Amersham Biosciences, Uppsala, Sweden). After local background substraction, average signal intensity from duplicate spots was normalized for differences in probe labelling using the values obtained for housekeeping genes (Bernard et al., 2002). For each gene, the OSM-induced modulation was expressed as the relative expression value for stimulated versus control sample. Arbitrarily, only modulation above 2 was considered significant for confirmation using RT-real time PCR assay.

Western Blotting Analysis

For STAT3 and MAPK phosphorylation, NHEK were stimulated for 15 min in the presence of the indicated cytokine. Cells were lysed in SDS sample buffer (62.5 mM Tris-HCl pH 6.8, 2% SDS, 10% glycerol, 50 mM DTT, 0.1% bromophenol blue), sonicated and then submitted to SDS-PAGE and transferred onto an Immobilon membrane. The membranes were subsequently incubated overnight with the primary antibody, before being incubated with the appropriate peroxidase-labelled secondary antibody for 60 min. The reaction was visualized by chemiluminescence according to the manufacturer's instructions. Membranes were stripped in 0.1 M glycine pH 2.8 for 2 h and neutralized in 1 M Tris-HCl pH 7.6 before reblotting. For neutralizing experiments, NHEK were incubated with the appropriate antibodies for 2 h before stimulation.

To determine the expression of gp130, LIFR and OSMR, the cells were lysed in 10 mM Tris HCl pH 7.6, 5 mM EDTA, 50 mM NaCl, 30 mM sodium pyrophosphate, 50 mM sodium fluoride, 1 mM sodium orthovanadate proteinase inhibitor and 1% Brij 96. After lysis and centrifugation to remove cellular debris, the supernatants were then treated as described above.

For S100 proteins expression, NHEK were stimulated for 2 days in the presence of OSM (10 ng/ml). Cell lysis was performed with 50 mM Tris HCl pH 7.4, 150 mM NaCl, 1 mM EDTA, 1% Triton, 1% sodium deoxycholate, 0.1%

SDS, 1 mM PMSF, 1 mM sodium orthovanadate, 1% protease inhibitors. S100A7, S100A8 and S100A9 were detected by immunochemistry as described above. Ponceau red staining was used to control loading homogeneity.

In Vitro Keratinocyte Migration Assay

Keratinocytes were cultured in wells pre-coated with type I collagen (200 µg/ml, Institut Jacques Boy, Reims, France) until they reached 80% confluency. Cells were starved for 48 h in Keratinocyte SFM and then treated with 10 µg/ml of mitomycin C (Sigma) for 2 h to prevent cell proliferation. A cell-free area was created by scraping the keratinocyte monolayer with a plastic pipette tip. Keratinocytes migration to the cell-free area was evaluated after 48 h of culture in the absence or presence of EGF or OSM. Using an inverted phase contrast microscope. The number of migrating keratinocytes was counted in 4 non-overlapping fields. Values represent the mean±SEM of cells per mm$^2$ beyond the frontiers of the in vitro injury. Student's t test was used for statistical analysis.

Reconstituted Human Epidermis Model

For histological and immunohistochemical studies, RHE, grown for 12 days at the air-medium interface, were purchased from SkinEthic Laboratories (Nice, France). They consist of a multi-layered epidermis which exhibit morphological and growth characteristics similar to human skin (Rosdy, Bertino et al. 1997). As recommended, RHE were grown for 1 day in SkinEthic growth medium prior to stimulation in the absence or presence of OSM for 4 days. They were then fixed in a balanced 10% formalin solution and embedded in paraffin. Four micron vertical sections were stained with heamatoxylin/eosin or with specific Ab and peroxidase-conjugated Antibodies, and counterstained with haematoxylin according to standard protocols (Rosdy, Bertino et al. 1997). Anti-K10 keratin and anti-filaggrin monoclonal Antibodies were from Lab Vision Corporation (Fremont, Calif., USA).

For gene expression profiling using cDNA macroarrays, 17 days old RHE were grown for 1 day in SkinEthic maintenance medium prior to stimulation in the absence or presence of OSM for 24 h. Total RNA was isolated and cDNA arrays were performed as described above.

Example 2: Human Keratinocytes Expressed the Type OSM Receptor on their Surface

Figure 1:
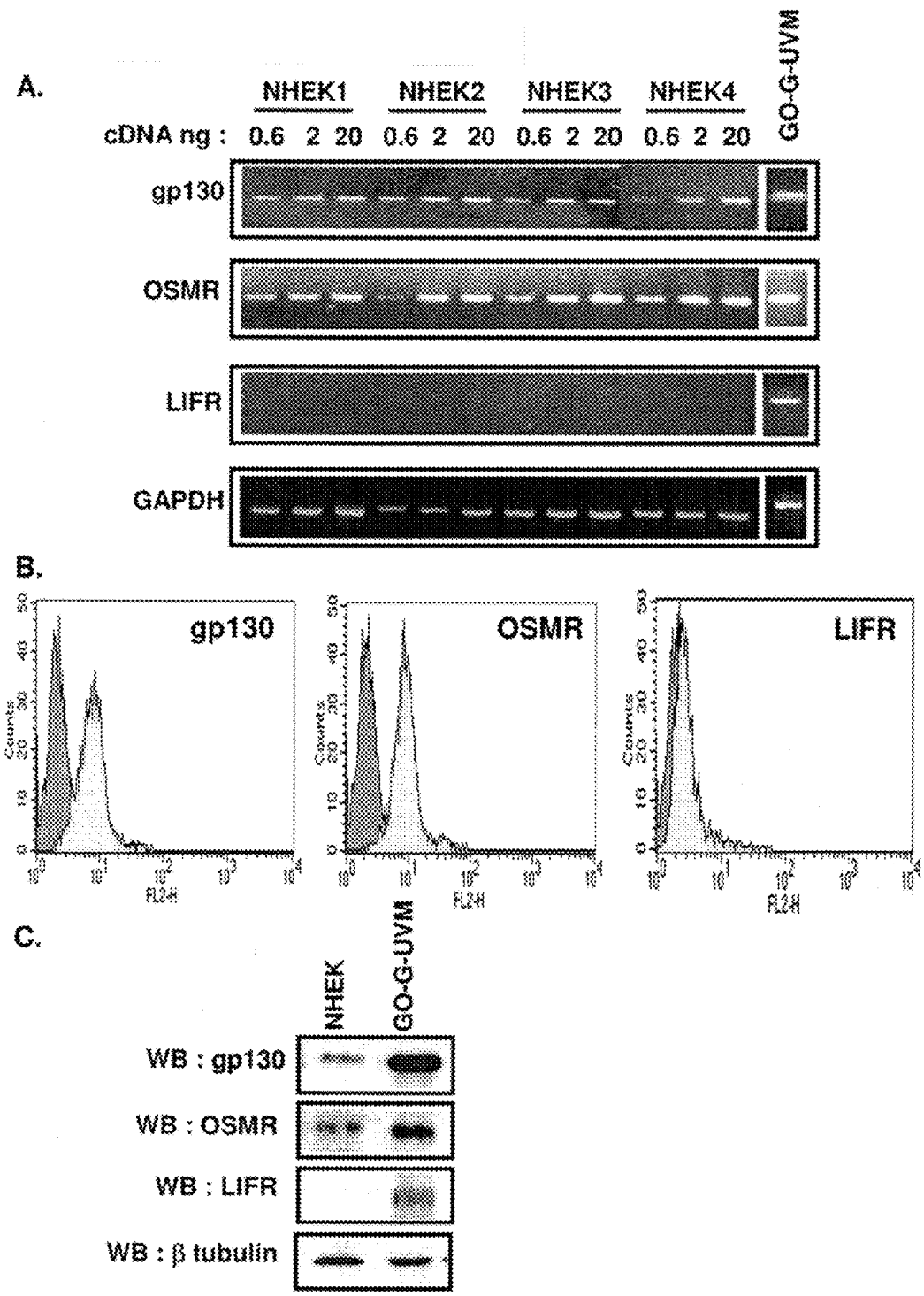
FIG. 1 shows the expression of OSM receptor by NHEK.

To show the potential functions of OSM in normal human keratinocytes the inventors first undertook an analysis of its receptor chain expression. To determine the nature of expressed type I or type II receptors, RT-PCR for gp130, LIFRβ and OSMRβ were carried out starting from primary cultures of keratinocytes. CO-G-UVM and glioblastoma cells were used as controls for LIFR. Obtained results show that NHEK predominantly expressed transcripts for OSMR and the gp130, whereas only low levels of the LIFR chain could be evidenced (FIG. 1A). The RNA analysis was further reinforced by measuring the expression levels of corresponding proteins by flow cytometry. Fluorescence analyses revealed a clear expression of gp130 and OSMRβ on the NHEK cell surface (FIG. 1B). In contrast no detection of membrane LIFRβ expression could be evidenced, whereas the anti-LIFRβ antibody gave the expected result when incubated with a cell line used as a positive control. This was further supported by western blot analyses showing the detection of gp130 and OSMRβ chains, and an absence of LIFRβ expression in NHEK (FIG. 1C). Similar experiments carried out on samples coming from four different donors led to the same results, ruling out the possibility for variations in type I or type II OSM receptor expression from donor to donor. These first results indicate that human keratinocytes preferentially expressed the specific type II OSM receptor.

Example 3: STAT-3 and MAP Kinase Pathways are Recruited by OSM in Human Keratinocytes The inventors show OSM-induced signal transduction in NHEK. Since STAT3 is usually recruited by the OSM type II receptor pathway, they analyzed the tyrosine phosphorylation of the signaling molecule in response to increasing concentrations of the cytokine. A strong induction of tyrosine phosphorylation was observed for STAT3, with plateau level values still present down to 3 ng/ml OSM (FIG. 2B). The involvement of gp130 and OSMRβ subunits was further demonstrated by blocking of the STAT3 phosphorylation when adding receptor neutralizing mAbs to the NHEK culture before OSM contact (FIG. 2C). Importantly, the complete neutralization of STAT3 phosphorylation observed in the presence of the anti-OSMRβ mAb further demonstrated the absence of recruitment by OSM of the share LIF/OSM type I receptor in NHEK. In agreement with this observation, after a LIF contact no evidence for a STAT3 activation could be observed in NHEK.

In addition, type II OSM receptor complex is also known to be a more potent activator for the recruitment of the Map kinase pathway compared to the shared LIF/OSM receptor. A cooperative effect between ERK1/ERK2 and the Shc adaptor, and mediated through OSMRβ, but not through the LIFRb, explains this strong activation the MAP kinase pathway in response to OSM (Boulton, Stahl et al. 1994). The ERK1/2 signaling in response to the cytokine in NHEK was therefore analyzed by determining their tyrosine phosphorylation level. As expected, NHEK stimulation with OSM quickly increased the MAP kinase phosphorylation (FIG. 2D). Taken together, these results demonstrated that gp130/OSMRβ receptor complex expressed in human keratinocytes is fully functional, and that the entire observed signals are mediated through the type II receptor.

Example 4: OSM is a Potent Inducer of Keratinocyte Migration

To underline the functional responses of NEHK to OSM, The inventors analyzed the potential effect of OSM on an in vitro model mimicking the wound healing and based on the keratinocyte migration (Kira, Sano et al. 2002). Forty eight hours after initiation of the culture, cells present in the middle of the well were removed by scratching, and the remaining keratinocytes were stimulated with either EGF, known to trigger the keratinocyte migration, or with OSM. After an additional 36 h of culture, the cytokine potential for inducing cell migration was visually determined or by cell counting (FIG. 3). Obtained results show that OSM led to an important migration of NHEK, similar to that observed in the presence of EGF.

Example 5: Identification of OSM-Induced Gene Expression in Human Keratinocytes

To have a better view of the NHEK functional response the inventors analyzed the modification of keratinocyte gene expression profile induced by OSM using cDNA arrays. Used arrays were specially designed for the study of keratinocytes, and consisting of 586 different cDNAs spotted in duplicate. They consisted in genes involved in keratinocyte cell structure, metabolism, extracellular matrix, adhesion, differentiation, signaling, signal transduction, apoptosis and stress (Bernard et al., 2002). RNA extracted from control or OSM-stimulated NHEK were used to generate labeled cDNA probes by reverse transcription. Probing the Atlas cDNA array membranes with these cDNA probes revealed that OSM increased the expression of 36 genes and decreased the expression of 38 genes. OSM down regulates a large set of genes associated with keratinocyte differentiation, such as cytokeratin (CK)1, CK10, fillagrin and loricrin genes. Among the up-regulated genes, the inventors found a marked increase for the calcium binding proteins, psoriasin (S100A7), calgranulins (S100A8, S100A9) and the S100 neutrophil protein (FIG. 4). Interestingly, the expression of these proteins is known to be up-regulated in inflammatory tissues (Madsen, Rasmussen et al. 1991; Nagase and Woessner 1999; Roth, Vogl et al. 2003). OSM also induced the G-protein-coupled receptor HM74, the super oxyde dismutase 2 and the beta-defensin genes, involved in tissue protection. Genes involved in tissue remodelling such as matrix metalloproteinase 1 and tenascin were also induced by OSM. In addition, OSM increased the expression of the chemokines CXCL1 (MIP-2α), CXCL5 (epithelial-derived neutrophil-activating peptide (ENA 78) and CXCL8 (IL-8), and the platelet-derived growth factor A (PDGF-A) genes.

Obtained results indicate that, in human keratinocytes, OSM was able to recruit a number of genes involved in inflammatory processes and in innate immune response.

Example 6: OSM Induced Keratinocytes to Produce Psoriasin, Calgranulin, β Defensin, and Chemokines To further reinforce the results obtained using designed-arrays, quantitative analyses at mRNA and protein levels were carried out for a selected number of identified genes. Quantitative analysis of psoriasin/S100A7 mRNA expression in response to OSM was performed by RT-real-time PCR along kinetic and dose-response studies. The inventors show that psoriasin/S100A7 mRNA was up-regulated in a dose-dependent manner in response to OSM ranging from 1.6 to 6.3 ng/ml after a 48-h treatment, and the plateau was reached for 6.3 ng/ml OSM with a fifty fold increase of the signal above control (FIG. 5A). Kinetic study revealed an increase in psoriasin/S100A7 mRNA expression starting at 12 h following stimulation with 10 ng/ml of OSM (FIG. 5B). It still increased up to 96 h, with a strong induction of about 290 folds above the control value. This was confirmed at the protein level by western blot analyses of the psoriasin/S100A7, as well as of two related calcium binding proteins, the S100A8 and S100A 9 calgranulins (FIG. 5D). Results show that NHEK exposure to 10 ng/ml of OSM resulted in an increased expression of studied proteins that was strongest at day 4 than at day 2 (FIG. 5D). FIG. 5C depicts the results obtained by analyzing the RNA quantitative expression of filagrin and βdefensin-2, two important markers of skin activation.

The production of the chemokines CXCL5 and CXCL8 in 48 h NHEK is also clearly enhanced under OSM stimulation (FIG. 6B).

Example 7: OSM Triggers Hyperplasia of Reconstituted Human Epidermis and Modulates the Expression of Differentiation Related Antigens To further approach the dynamic of epidermal differentiation, the inventors tested the biological effect of OSM on in vitro RHE in order to assess the basal cell layer proliferation and the graduated epidermal differentiation processes. Histological analysis of control RHE showed a keratinised multi-stratified epithelium resembling epidermis in vivo, containing intact basal, spinous, granulous and cornified cell-layers, and numerous keratohyalin granules in the upper granular layer (FIG. 7). OSM triggered the hyperplasia of the keratinocytes layers, leading to an increase in the overall thickness of the RHE. In addition, they observed a loss of keratohyalin granules in the granular layer and the presence of picnotic nuclei. cDNA array profile analysis of RHE confirmed that OSM strongly up-regulated S100A7, S100A8, S100A9 and S100 neutrophil protein genes, as previously described on NHEK (FIG. 4). By immunohistochemistry, we confirmed the S100A7 protein up-regulation in OSM-treated RHE (FIG. 7). In agreement with the data on NHEK, OSM treatment on RHE also up-regulated CXCL5, CXCL8 chemokine genes, and the PDGF-A and the cadherin 3 gene transcription. Specific to RHE but not detected in NHEK, OSM up-regulated the CK6A, 6B, 6D, 7, 13, 14, 16, the skin-derived antileukoproteinase and the TGFβ-inducible early protein.

On the other hand, OSM down-regulates genes associated with keratinocyte differentiation, such as involucrin, filaggrin, and calmodulin-like skin protein (Mehul, Bernard et al. 2000; Rogers, Kobayashi et al. 2001; Jonak, Klosner et al. 2002; Wagener, van Beurden et al. 2003) Immunohistochemical analysis performed on RHE sections confirmed the inhibition of keratinocyte differentiation, as indicated by the decrease of filaggrin and keratin 10 expression in OSM treated RHE (FIG. 7).

Example 8: Discussion

The use of a cDNA array approach, specially designed for the analysis of gene expression in human skin, enabled the identification of OSM target genes in human keratinocytes and the demonstration of the involvement of OSM in a variety of processes, including migration and differentiation. In particular, the strong, dose dependent, OSM-mediated induction of the expression of S100A7, S100A8 and S100A9 proteins in NHEK and RHE demonstrates the pro-inflammatory and chemotactic effects of the cytokine. The opposing effects of IL-10 and OSM in cutaneous inflammation are underscored by the IL-10-induced down-regulation of S100A8 and S100A9 release by monocytes (Lugering, Kucharzik et al. 1997). S100A7, S100A8 and S100A9 belong to the pleiotropic S100 family of calcium-binding proteins (Roth, Vogl et al. 2003). Although their main functions are as yet unclear, they appear to play prominent inflammatory functions (Watson, Leygue et al. 1998; Donato 1999; Roth, Vogl et al. 2003) and to be involved in the tight regulation of a large number of intra and extracellular activities such as the dynamic of motility of cytoskeletal components or chemotaxis (Ryckman, Vandal et al. 2003). Interestingly, whereas all three S100A7, S100A8 and S100A9 proteins have been reported to be expressed at low or undetectable levels in normal skin epidermis and non-differentiated cultured keratinocytes, they are highly expressed in abnormally differentiated psoriatic keratinocytes (Broome, Ryan et al. 2003), during wound repair (Thorey, Roth et al. 2001) and in epithelial skin tumors (Watson, Leygue et al. 1998; Gebhardt, Breitenbach et al. 2002; Alowami, Qing et al. 2003). Because of the chemotactic effects of S100A7 on inflammatory cells, in particular neutrophils and CD4$^+$ T lymphocytes, it has been suggested that S100A7 may be involved in the genesis of psoriatic lesions (Watson, Leygue et al. 1998). Since S100A7 acts upstream of these mechanisms, the inventors demonstrate that OSM is a key molecule for the induction of S100A7 under pathological conditions, and is involved in the pathological state. The modulation of additional genes by OSM is also in favour of the pro-inflammatory and chemotactic roles of OSM. Indeed, the induction of neutrophil attractant chemokine CXCL5/ENA-78 together with the down-regulation of heme oxygenase 1, which antagonizes inflammation by attenuating adhesive interaction and cellular infiltration in skin, could contribute to the neutrophil influx in skin (Koch, Kunkel et al. 1994; Wagener, van Beurden et al. 2003).

OSM-induced MMP-3 expression is also of interest in the context of inflammatory cutaneous diseases and wound repair. Whereas MMP-3 cannot be detected in normal skin, it is expressed by proliferative keratinocytes of the basal layer after injury (Pilcher, Wang et al. 1999). During progression of many diseases, MMP-3 is involved in epidermis remodeling by removal of extracellular matrix during tissue resorption (Nagase and Woessner 1999; Pilcher, Wang et al. 1999), and mice that lack the MMP-3 gene are deficient in wound repair of the epidermis (Bullard, Lund et al. 1999). Using an in vitro wound assay, the inventors demonstrated that keratinocyte migration is strongly increased by OSM stimulation. These data are in agreement with the demonstration that STAT3 deficiency in keratinocytes leads to an impaired migration (Sano, Itami et al. 1999). Under inflammatory conditions, OSM appears to be one essential mediator enhancing keratinocyte migration and wound healing, via MMP-3 or S100A8-S100A9 dependent mechanisms. Additional evidence to establish the involvement of OSM in wound healing is the strong induction of PDGF in RHE, a major proliferative and migratory stimulus for connective tissue during the initiation of skin repair processes (Rollman, Jensen et al. 2003).

The inventors also showed that OSM increases the overall thickness of the keratinocyte layer of RHE. This process seems not to be related to basal cell hyperproliferation since Ki67 expression is not induced in response to OSM, but more likely results from an inhibition of terminal keratinocyte differentiation, as shown by the decreased production of filaggrin, loricrin or involucrin. OSM down-regulates the expression of the calmodulin-like skin protein (CLSP) and calmodulin-related protein NB-1, two members of the calmodulin family, directly related to keratinocyte differentiation (Mehul, Bernard et al. 2001; Rogers, Kobayashi et al. 2001). CLSP binds transglutaminase-3, a key enzyme implicated in the formation and assembly of proteins, such as loricrin or involucrin, to form the cornified cell envelop of the epidermis (Mehul, Bernard et al. 2000). The modulating effects of OSM on the keratin expression profile, i.e., keratin 6 over-expression and keratin 10 inhibition, also supports the notion of an inhibition of epidermal differentiation. Keratin 6 is known to be induced under hyperproliferative and/or inflammatory situations, including wound healing, psoriasis, carcinogenesis, or by agents such as retinoic acid that provoke epidermal hyperplasia (Navarro, Casatorres et al. 1995; Komine, Rao et al. 2000). In contrast, keratin 10, normally expressed in terminally differentiating epidermal keratinocytes, is reduced during wound healing (Paramio, Casanova et al. 1999).

Example 9: Similar Results Obtained with IL-31

Studies presented in examples 3, 4 and 5 have been realized with IL-31 instead of OSM and similar results were obtained: IL-31 recruits STAT3 signaling pathways (FIG. 8) in NHEK and induces expression of psoriasin (S100A) and calgranulin A and B (S100A8-9) (FIG. 9). IL-31 is also able to induce keratinocyte migration (FIG. 10).

Example 10: Gamma Interferon Potentiates the Action of IL-31 on the Signal Transduction When NHEK were preincubated 24 h in the presence of 50 g/ml of gamma Interferon (INFγ) before IL-31 stimulation (50 ng/ml), P-STAT3 level were increased 3 to 4 folds when compared to NHEK preincubated in medium alone (same studies as those realized for the FIG. 8). This demonstrates that INFγ is a modulator of the action of IL-31 on signal transduction.

Example 11: IL-17 and TNFα Potentiate the Action of OSM on the Expression of Several Inflammation Markers The combined effect of several cytokines on keratinocytes was then tested by measuring the expression of the keratinocyte inflammation markers psoriasin (S100A7), defensin beta-2/beta-4 (hBD2/4) mRNAs, in the presence of various cytokines cocktails. The effect of these cocktails was also tested on keratin 10 (KRT10) mRNA, since KRT10 is a differentiation marker associated with tissue healing.

To that aim, confluent normal human keratinocytes (NHEK) were treated for 24 hrs with the indicated mix of cytokines (each cytokine at 1 ng/ml final concentration). Total RNA was extracted, reverse-transcribed and the expression of the selected genes was analyzed by real-time PCR as described.

The results are shown in Table 1 below and in FIG. 11.

TABLE 1

| | cytokines 1 ng/ml | | | RT-Q-PCR | | | X/GAPDH | | |
|---|---|---|---|---|---|---|---|---|---|
| #mix | IL-22 | OSM | IL-17 | TNFα | IL-1α | IFNγ | S100A7 | hBD2/4 | KRT10 |
| M3 | + | + | + | + | + | + | 6 350 | 1 441 000 | 36 |
| M1 | + | + | + | + | − | + | 5 450 | 1 380 000 | 38 |
| M4 | + | + | + | + | + | − | 7 270 | 1 185 000 | 30 |
| M8 | − | + | + | + | + | − | 7 880 | 1 165 000 | 36 |
| M7 | + | − | + | + | + | − | 2 550 | 475 000 | 51 |
| M6 | + | + | − | + | + | − | 1 610 | 32 585 | 45 |
| M5 | + | + | + | − | + | − | 2 450 | 211 000 | 49 |
| M2 | + | + | + | + | − | − | 6 570 | 1 331 000 | 40 |
| | − | − | − | − | − | − | 100 | 100 | 100 |

The mix of the 6 selected cytokines (M3) exhibited a strong synergic effect on the expression of the keratinocyte inflammation markers psoriasin (S100A7) and defensin beta-2/beta-4 (hBD2/4). As expected, KRT10 expression is lowered in the presence of these cytokines. The depletion of the mixes in either IFNγ, IL-22, or IL-1α, did not significantly decrease the activity of the complete cocktail of cytokines; these cytokines are hence probably not directly involved in the observed synergy. To the contrary:

the omission of OSM from the 5 cytokines reference mix (IFN' has been omitted because it is inactive) led to a decrease of the activity of the mix by 3-fold for S100A7 and by 2.5-fold for hBD2/4;

the omission of TNFα led to a decrease of the activity of the mix by 3-fold for S100A7 and by 5.6-fold for hBD2/4; and the omission of IL-17 led to a decrease of the activity of the mix by 4.5-fold for S100A7 and by 36-fold for hBD2/4.

These results indicate a strong synergy between OSM, TNFα and IL-17 for a maximal response in keratinocytes.

Hence, it appears that OSM is able to synergize with IL-17 and/or with TNFα. In addition, it is suggested that OSM may act synergistically with IL-17 and/or with TNFα for the acceleration of wound re-epithelialization, even at low cytokine concentrations.

Example 12: OSM Improves the Cutaneous Innate Immune Response

Keratinocytes in the skin of patients with psoriasis produce high levels of anti-microbial peptides (Nomura, Goleva et al. 2003). These peptides, present only at negligible levels in normal skin or in the skin of patients with atopic dermatitis, are essential in the cutaneous innate immune response to invading microorganisms, as shown in animal models of infection (Nizet, Ohtake et al. 2001). The enhanced S100A7-psoriasin gene expression in keratinocytes, following stimulation with OSM, therefore points to a role for OSM in the cutaneous innate immune response, as S100A7-psoriasin has been shown to confer resistance to infection of the skin by *Escherichia coli* (Glaser, Harder et al. 2005). Similarly, β-defensin 2, another protein with anti-microbial activities (Harder, Bartels et al. 1997), is induced by OSM in human keratinocytes. Beta-defensin 2 is expressed at high levels in psoriatic lesions but only at low levels in those observed in atopic dermatitis (Ong, Ohtake et al. 2002). In line with this observation, psoriatic patients are reportedly less susceptible to infections, as compared with patients having atopic dermatitis (Nomura, Goleva et al. 2003).

The results reported in Examples 6 and 11 above hence show that OSM, IL-17 and TNFα are potent keratinocyte activators, and that topic administration of these cytokines, either alone or in combination, can enhance the expression of anti-microbial peptides and improve the cutaneous innate immunity.

Example 13: Skin Inflammation Induced by the Synergistic Action of IL-17A, IL-22, OSM, IL-1α and TNFα Recapitulates Some Features of Psoriasis 13.1. Materials and Methods Skin Samples The use of skin samples for this study was approved by the Ethical Committee of the Poitiers Hospital. After informed consent, lesional skin biopsies were obtained from eight different patients with moderate to severe plaque psoriasis (mean age=47 years; skin involvement 30-90% of body surface area) that did not receive any therapy for >4 wk. Normal skin biopsies were obtained from surgical samples of healthy breast skin.

Cell Cultures, Cytokines and Reagents

NHEK were obtained as previously described, from surgical samples of healthy breast skin (Boniface et al, 2005). NHEK were cultured to 80% of confluence and then starved for 24 h in Keratinocyte SFM without addition of growth factors before stimulation. Cells were stimulated with or without 10 ng/ml of recombinant IL-17A, OSM, TNFα, IL-22 and IL-1α alone or in combination (R&D systems Europe, Lille, France) during 24 h for mRNA quantification or 48 h to 96 h for protein quantification.

In Vivo Murine Skin Inflammation

Outbred OF1 mice were purchased from Charles River Laboratories (Chatillon, France). Ear intradermally injections were realized at day 0 under brief isoflurane (Forene, Abott France, Rungis, France) gas anesthesia. 250 ng of carrier free IL-17A, OSM, TNFα, IL-22 and IL-1α (R&D systems Europe) or PBS or 10 µg of LPS (Sigma-Aldrich, Saint Quentin Fallavier, France) were injected in a total volume of 20 µL. After 24 or 48 h, ears were collected and frozen immediately in liquid nitrogen for H&E staining, immunohistochemistry analysis or RNA quantification.

Ex Vivo Human Skin Culture

Pieces (2×2 cm) of healthy breast skin were washed in PBS and intradermally injected with 10 ng of each cytokines (IL-17A, OSM, TNFα, IL-22 and IL-1α) or with PBS 0.1% BSA in a total volume of 50 µl. Each sample was placed individually in a 6-well plate and incubated up to 72 h at 37° C., 5% $CO_2$, in SkinEthic maintenance medium (SkinEthic Laboratories, Nice, France). Punch biopsy of 4 mm was taken after 24 h of treatment at the site of injection and immediately frozen in liquid nitrogen for RNA quantification. Culture supernatants were collected for cytokine ELISA determination.

Macroarrays Analysis

The comparison of the effects of 36 different cytokines on the expression of 154 genes of potential interest for skin physiology was performed using home-made cDNA macroarrays analysis. After cytokine stimulation, total RNA was extracted using TRIzol® Reagent (Invitrogen life Technologies) and conventional 33P-cDNA target synthesis and hybridization were performed (Boniface et al, 2007). Genes were considered regulated if expression levels differed more than 3-fold relative to untreated control and 3-fold relative to mean background noise.

RT-Real Time PCR Analysis

NHEK and skin total RNA were isolated and reverse-transcribed as previously described (Boniface et al, 2005). Quantitative real time PCR was carried using the LightCycler-FastStart DNA Master SYBR® Green I kit on LightCycler 480 (Roche Diagnostics, Meylan, France). The reaction components were 1×DNA Master Mix, and 0.5 µM of HPLC purified sense and anti-sense oligonucleotides purchased from Eurogentec (Eurogentec France, Angers, France), designed using Primer3 software. Samples were normalized to three independent control housekeeping genes (G3PDH, RPL13A or ACTB for human samples and G3PDH, HMBS or B2m for mouse samples) and reported according to the $\Delta\Delta C_T$ method as RNA fold increase: $2^{\Delta\Delta CT} = 2^{\Delta CT\ sample - \Delta CT\ reference}$. For comparison of normal skin and psoriatic skin the REST 2008 software was used (Pfaffl et al., 2002).

Cytokine Measurement by ELISA

Levels of BD2, BD3 and CXCL8 were determined using Human ELISA development kit (Peprotech), and CXCL1 and CXCL5 with DuoSet reagents (R&D Systems Europe).

Western Blotting Analysis

After 96 h of stimulation, NHEK lysis was performed as previously described (Boniface et al, 2005). After separation by SDS-PAGE, proteins were transferred to nitrocellulose membranes (Amersham pharmacia biotech) by electroblotting. S100A7 was detected with mouse anti-human S100A7 mAb (Imgenex, San Diego, Calif., USA) and sheep anti-mouse IgG peroxidase-conjugated polyclonal Ab (Amersham Biosciences). Bound Ab were detected by chemiluminescence (ECL Hyperfilm and ECL Plus Reagen, Amersham Biosciences Ltd).

Chemotaxis Assay

Chemotaxis assay was performed using 24-well transwell inserts (transparent polyethylene terephthalate membrane, 3-nm pore; Becton Dickinson Biosciences, Le Pont de Claix, France). Human neutrophils obtained from peripheral blood of healthy volunteers were labelled with 5 μM Calcein AM (Molecular Probes, Invitrogen Life Technologies). NHEK culture supernatants were incubated or not with anti-CXCL8 (10 μg/ml), anti-CXCL1/2/3 and/or anti-CXCL5 mAb (25 μg/ml) (All from R&D systems) for 30 min at 37° C. Four hundred μl of NHEK supernatants were added to the lower chamber of a Transwell plate and 200 μl of calcein-labelled neutrophils were added to the upper chamber. After incubation 2 h at 37° C., 5% $CO_2$, the number of migrating cells in the lower chamber was determined by measuring calcein fluorescence. Results are expressed as percentage of migrating neutrophils per well.

Assay for Anti-Bacterial Activity

Supernatants from NHEK treated or not for 96 h with cytokines were 50 fold concentrated by centrifugation using Amicon Ultra 3000 Da (Millipore, Saint-Quentin en-Yveline) and dialysed against sodium phosphate buffer (10 mM, pH 7.4). *Escherichia coli* (American Type Cell Collection 29325) was grown to exponential phase, bacterial concentration was adjusted to $2 \cdot 10^5$ bacteria/ml in 10 mM sodium phosphate buffer and mixed (ratio 2:1) with concentrated NHEK supernatants or with human recombinant BD2 (Peprotech). After incubation at 37° C. for 1 h, serial dilutions of bacterial suspensions were plated onto Brain Heart Infusion agar plates and cultured for 24 h at 37° C. for determination of bacterial CFU. Results are expressed as percentage of CFU in control condition with the mean and SEM of three independents experiments.

Histological Studies and Immunohistochemistry for Gr-1

Six μm-sections of mouse ear were fixed in 10% formalin in PBS. Ear thickness was measured after H&E coloration at 3 different points in the injection area. Standard deviation from the mean is shown for 3 separate experiments.

Sections of mouse ear were stained for granulocytes by using rat IgG2b anti-mouse Ly-6G mAb (Gr-1, Becton Dickinson Biosciences) or with isotype control (IgG2b, Caltag, Invitrogen Life Technologies) associated with a donkey anti-rat IgG Alexa Fluor 488-conjugated secondary antibody (Invitrogen Life Technologies). Confocal microscopy was carried out on a Olympus FV1000 confocal. Pictures are representative of 3 experiments.

Statistics

Statistical analysis of significance was calculated using either Mann-Whitney or Kruskal Wallis one way analysis of variance by ranks with a Dunn's test. P values of 0.05 or less were considered as significant, and all data are represented as mean and SEM. Comparison study used the Spearman rank correlation test.

13.2. Results

Identification of Cytokines Able to Modify Keratinocyte Transcriptional Profile

In order to identify major skin inflammation inducers we screened the activity of 36 different cytokines previously described for their effect in the skin or for their involvement during regulation of the immune/inflammatory response. We compared their effects on the expression of 154 genes of potential interest for skin physiology. Among the cytokines able to modify the expression of at least five genes (with at least a three fold increase or decrease), we identified IL-22, IL-24, IL-6, OSM, IL-1α, IL-1β, TNFα and IL-17A (FIG. 12).

IL-1α, IL-17A, IL-22, OSM, and TNF-α Strongly Induce BD2 and CXCL8 Production by Keratinocyte We further selected the most potent cytokine from each family, based on the number of genes regulated and on the fold increase or decrease gene expression i.e. IL-1α, IL-17A, IL-22, OSM and TNF-α (named M5 combination in the present example) and showed their strong synergistic activity on the production of BD2 (161900 pg/ml vs 85 pg/ml for control culture) and CXCL8 (41800 pg/ml vs 80 pg/ml) (FIG. 13A). By successive removal of each cytokine of the M5 combination and replacement by a cytokine of the same family, we identified major contributors of keratinocyte inflammation and analyzed cytokine redundancy. IL-17A and TNF-α were more critical to the activity of the M5 combination than IL-1α, OSM, or IL-22 on BD2 and CXCL8 production (FIG. 13B). Substitution by cytokines of the same family demonstrated a total redundancy between IL-1α and IL-1β, strong redundancy between TNFα and TNFβ, limited redundancy between IL-17A and IL-17F, IL-22 and IL-24 and weak redundancy between OSM and IL-6 (FIG. 13B).

Ex Vivo and In Vivo Pro-Inflammatory Activities of the Cytokine Mix

In order to evaluate the pro-inflammatory activities of the M5 cytokine combination in the skin, we setup human ex vivo and murine in vivo skin challenges. Human normal skin explants were injected with the M5 cytokine mix and cultured for 24 h before S100A7, CXCL8, and BD2 mRNA quantification. A strong increase of S100A7, CXCL8, and BD2 gene transcription was observed after injection of the M5 combination when compared to the saline-injected or non-injected skin explants (FIG. 14). BD2 quantification by ELISA in the skin explants culture supernatants confirmed the ten to hundred fold increased in BD2 production over a three day culture period (FIG. 14).

To assess in vivo the effect of the pro-inflammatory cocktail, the M5 cytokine combination was injected intradermally in mouse ears in parallel to LPS which was used as a positive control. After 48 h, redness and swelling were observed in M5-injected ears as well as a two-fold increase in ear thickness in comparison to saline-injected ears (FIGS. 15A and 15B). Interestingly, histological analysis revealed an important inflammatory cellular infiltrate in ears injected with M5, comparable to the one obtained in LPS-injected ears Immunohistological analysis with anti-Gr1 mAb revealed abundant granulocytes in ear tissue from LPS- or M5-injected mice compared to saline-injected mice (FIG. 15A). This infiltrate was predominantly present in the dermis and associated with an increase in CXCL1, CXCL3, and to a lesser extent CXCL2 gene transcription. In addition, transcription of the antimicrobial peptide encoding genes S100A9 and BD3 was strongly induced by the M5 combination (FIG. 15B).

Modification of Keratinocyte Transcriptional Profile Induced by Pro-Inflammatory Cytokine Combination In order to further characterize the activity of the cytokine mix on innate immunity, the antimicrobial peptides and chemokines transcriptional profile was determined by RT-QPCR analysis. The transcription of nine chemokines and 12 antimicrobial peptides encoding genes was upregulated in response to the M5 combination (FIG. 16). Among these 21 genes, expression of 19 was upregulated by IL-1α, 16 by IL-17A, 20 by TNFα, 14 by IL-22, and 13 by OSM (FIG. 16). A strong transcriptional synergy with the M5 cytokine combination was observed for BD2, BD3, LL37, RNASE7, PI3, S100A7, S100A7A, S100A12, CXCL1, CXCL2, CXCL3, CXCL5, CXCL6, and CXCL8 whereas only an additive effect of M5 was observed for S100A8, S100A9, CCL5, CCL20, WFDC5, and WFDC12. Finally, the activity of the M5 combination on CCL27 gene transcription seems to be due to the redundant activity of IL-1α and TNFα (FIG. 16).

Production of CXCL Chemokines and Chemotactic Activity

We further examined the production of CXCL1, CXCL5, and CXCL8 proteins by ELISA. As shown in FIG. 17A, untreated NHEK secreted low levels of CXCL1, CXCL5, and CXCL8. IL-1α was the most effective followed by IL-17A or TNFα, and finally IL-22 or OSM with a discrete effect on chemokine production. However, in combination, IL-17A, OSM, TNFα, IL-22, and IL-1α synergistically induced a massive secretion of CXCL1, CXCL5, and CXCL8 with induction factors of 190, 80 and 650 respectively when compared to controls (FIG. 17A).

We next analyzed the chemotactic activity of supernatants from control or stimulated NHEK. Supernatants from M5-stimulated NHEK had a significantly increased chemotactic activity for neutrophils compared to supernatants from unstimulated cultures (FIG. 17A). Neutrophil chemotactic activity was significantly reduced when neutralizing the activities of CXCL1/2/3 or CXCL5, and totally blocked when inhibiting CXCL8 (FIG. 17A).

Antimicrobial Peptides Production and Activity

Since we showed that antimicrobial peptide gene expression was strongly induced after NHEK stimulation by the M5 combination, we further quantified BD2 and BD3 protein by ELISA in NHEK supernatants. As shown in FIG. 17B, BD2 was significantly induced by the five cytokines alone, amongst them IL-1α and IL-17A being the most potent inducers. A strong synergy was seen with the M5 combination with an induction factor of 24,000 when compared to unstimulated keratinocytes. A significant increase of BD3 production was seen for IL-1α, IL-22, or OSM stimulation. Here again, the M5 combination resulted in a strong synergistic effect on BD3 production (FIG. 17B), in agreement with previously observed increased gene transcription.

Expression of S100A7 in NHEK was evaluated by western blotting analysis. S100A7 was barely detected in unstimulated NHEK (FIG. 17B). Each of the five cytokines alone induced S100A7 production, IL-1α being the most potent inducer, and a stronger expression was observed when the M5 combination was used.

We next evaluated the antimicrobial activity of M5-stimulated NHEK culture supernatants against E. coli, and showed that they exhibited strong antibacterial activity compared to the unstimulated NHEK supernatants. A similar activity for recombinant BD2 was observed (FIG. 17B).

Transcriptional Profile of Lesional Psoriatic Human Skin

In order to evaluate the pathophysiological relevance of the inflammatory phenotype observed in vitro when stimulating NHEK with the M5 combination, we quantified the gene expression of several proinflammatory cytokines and their potential targets, in particular chemokines and antimicrobial peptides, in normal skin and psoriatic skin. We were able to detect overexpression of IL-23, IL-17A, IL-22, and OSM in psoriatic skin as compared to normal skin, as well as a small increased expression of IL-1α, whereas IL-1α and TNFα expression were not different. Among the 12 antimicrobial peptides analyzed, the transcription of 10 of them was higher in psoriatic skin compared to normal skin, with more than 100 fold increases for BD2, S100A7A, S100A12, PI3, S100A7, S100A9, and S100A8 (Table 2). Expression of CXCL8, CXCL1, CXCL6, CCL20, CXCL5, and CCL5 encoding genes was also strongly increased in psoriatic skin compared to normal skin, but CCL27 expression was lower (Table 2). In summary, among the 21 genes overexpressed in our in vitro model, the expression of 18 was higher in psoriatic skin compared to normal skin, and a correlation was found between these two sets of data (FIG. 18).

TABLE 2

Transcriptional profile of psoriatic skin versus normal skin

| Gene | Ratio Psoriasis/Control[a] | p Value[b] |
|---|---|---|
| Cytokine | | |
| IL-17A | 24 | <0.001 |
| IL-23 | 16 | <0.001 |
| IL-22 | 16 | 0.004 |
| OSM | 5 | 0.003 |
| IL-1β | 2.4 | 0.131 |
| TNF-α | 0.8 | 0.342 |
| IL-1α | 0.8 | 0.537 |
| Chemokine | | |
| CXCL8 | 38 | 0.002 |
| CXCL1 | 38 | 0.001 |
| CXCL6 | 26 | 0.001 |
| CCL20 | 19 | 0.001 |
| CXCL5 | 9 | 0.003 |
| CCL5 | 3.2 | 0.022 |
| CXCL3 | 2.4 | 0.433 |
| CXCL2 | 2.3 | 0.487 |
| CCL27 | 0.03 | 0.001 |
| Antimicrobial peptide | | |
| BD2 | 5962 | <0.001 |
| S100A7A | 1804 | <0.001 |
| S100A12 | 792 | 0.001 |
| PI3 | 934 | <0.001 |
| S100A7 | 224 | 0.001 |
| S100A9 | 305 | 0.001 |
| S100A8 | 287 | 0.001 |
| LL37 | 16 | 0.001 |
| WFDC12 | 5 | 0.004 |
| RNase7 | 3 | 0.007 |
| BD3 | 1.6 | 0.170 |
| WFDC5 | 0.7 | 0.313 |

Example 14: Inhibition of Keratinocyte Differentiation by the Synergistic Effect of IL-17A, IL-22, IL-1α, TNFα and Oncostatin M 14.1. Materials and Methods Skin Samples The use of human skin samples for research studies was approved by the Ethical Committee of the Poitiers Hospital. The Declaration of Helsinki protocols were followed and patients gave their written informed consent. Biopsies were obtained from the back skin lesions of 5 different patients with moderate to severe plaque psoriasis (mean age=45 years; PASI>10) that did not receive any therapy for >4 wk. Normal skin biopsies were obtained from surgical samples of healthy breast skin.

Cell Cultures, Cytokines and Reagents

Normal human epidermal keratinocytes (NHEK) were obtained as previously described, from surgical samples of healthy breast skin (Boniface et al, 2005). NHEK were cultured to 80% of confluence allowing the expression of a large panel of keratinocyte differentiation markers, and then starved for 24 h in Keratinocyte SFM containing 0.03 mM $Ca^{2+}$ (Invitrogen Life Technologies, Cergy Pontoise, France) before stimulation. Confluent differentiated cells were stimulated with or without recombinant IL-17A, OSM, TNFα, IL-22 and IL-1α alone at maximum effective concentrations (reported previously around 10 ng/ml (Boniface et al, 2005 and Boniface et al, 2007)) or in combination (R&D systems Europe, Lille, France) during 2 h to 72 h for mRNA quantification. RHE were generated on polycarbonate culture inserts, from surgical samples of paediatric foreskins as previously described (Guenou et al., 2009). RHE were stimulated with or without recombinant IL-17A, OSM, TNFα, IL-22 and IL-1α alone or in combination, with or without a Janus protein Tyrosine Kinases (JAKs) inhibitor 10 μM (Calbiochem, 420099), during 24 h for mRNA quantification or during 72 h for immunohistological analysis.

In Vivo Murine Skin Inflammation

All animal experiments were conducted in accordance with the guidelines and approval of the Institutional Animal Care and Usage Committee at the University of Poitiers. C57Bl/6 mice were purchased from Charles River Laboratories (Chatillon, France). Ear intradermal injections were performed under brief isoflurane (Forene, Abott France, Rungis, France) gas anesthesia. 250 ng of carrier free IL-17A, OSM, TNFα, IL-22 and IL-1α (R&D systems Europe) or PBS were injected in a total volume of 20 μL. After 24 or 48 h, the ears were collected and frozen immediately in liquid nitrogen for H&E staining, immunohistochemistry analysis or mRNA quantification.

RT-Real Time PCR Analysis

NHEK, RHE and murine skin total RNA were isolated using NucleoSpin® RNA II kit (Macherey-Nagel, Hoerdt, France) and reverse-transcribed with SuperScript® II Reverse Transcriptase (Invitrogen Life Technologies) according to the manufacturer's instructions. Quantitative real time PCR was carried out using the LightCycler-FastStart DNA Master SYBR® Green I kit on LightCycler 480 (Roche Diagnostics, Meylan, France). The reaction components were 1×DNA Master Mix, and 0.5 μM of HPLC purified sense and anti-sense oligonucleotides purchased from Eurogentec (Eurogentec France, Angers, France), designed using Primer3 software. The stability of the housekeeping gene expression has been assessed by using GeNorm algorithm. The GeNorm software calculates the M value expression stability for the candidate reference genes and considers the gene with the lowest M value to have the most stable expression (Vandesompele et al., 2002). The lowest M value for G3PDH demonstrates that the expression is stable under the conditions used for NHEK, RHE and in vivo stimulation. Thus samples were normalized to G3PDH housekeeping gene and reported according to the $\Delta\Delta C_T$ method as RNA fold increase: $2^{\Delta\Delta CT} = 2^{\Delta CT\ sample - \Delta CT\ reference}$.

Histology and Immunohistochemistry Studies

Six μm cryosection of ears from mice or human skin were fixed in 10% formalin in PBS. Sections of ears were stained with anti-CK10 1:500 (Covance, PBR-159P), anti-LOR 1:500 (Eurogentec, PRB-145P), anti-FLG 1:200 (Covance, PRB-417P), anti-CK6 1:250 (ThermoScientific, PA1-29671) and anti-Ki67 1:100 (DakoCytomation) associated with a donkey anti-rat IgG FITC-conjugated secondary antibody or anti-rabbit IgG Rhodamine Red™-X conjugated antibody (Jackson Immunoresearch). Cell nuclei were detected with TOPRO 3 1:800 (Invitrogen). Confocal microscopy was carried out on a Olympus FV1000 confocal.

Human skin sections were stained with anti-CK10 1:100 (SantaCruz, SC-23877), anti-LOR 1:50 (Eurogentec, PRB-145P), anti-FLG 1:100 (SantaCruz, SC-66192), anti-IVL 1:20 (Biomedical Technologies, BT-601), anti-S100A7 1:50 (Clinisciences, IMG-409A), and then detected using a biotin-conjugated secondary antibody (Vector, RTU vectastain universal quick kit, PK-7800) and the chromatic substrat AEC (Dako, Substrat hyper-sensible AEC+).

RHE were washed and fixed with formaldehyde solution. Fixed tissues were dehydrated with increasing ethanol concentrations, embedded in paraffin and sections were carried out using a microtome (4 μm thickness). The sections were deparaffinised, washed and incubated with hydrogen peroxide. The sections were incubated with anti-CK10 (SantaCruz, SC-23877), anti-LOR (Eurogentec, PRB-145P), anti-FLG (SantaCruz, SC-66192), anti-IVL (Biomedical Technologies, BT-601), anti-S100A7 (Clinisciences, IMG-409A) and then detected using a biotin-conjugated secondary antibody (Vector, RTU vectastain universal quick kit, PK-7800). After peroxidase-conjugated streptavidine (Vector, RTU vectastain universal quick kit, PK-7800) and peroxidase substrate addition (Dako, Substrat hyper-sensible AEC+), nuclei were counter-stained using a solution of hematoxylin. Sections were observed using a NIKON E400 microscope. The images were captured using a NIKON DS-Ril and processed with NIS-Elements 3.10 software.

Statistics

One-way ANOVA with a Dunnett post-test or Mann-Whitney test were used for the statistical evaluation. The p values were as follows: *$p<0.05$, $p<0.01$, *$p<0.001$, and all data are represented as mean and SEM.

14.2. Results

Synergistic Activity of Proinflammatory Cytokines on Inhibition of KDM Expression by Normal Human Epidermal Keratinocyte The activities of IL-1α, IL-17A, IL-22, OSM and TNFα have been studied on keratinocyte differentiation markers (KDM) expression based on previous reports showing their inflammatory activities on keratinocyte (Boniface et al, 2005 and Boniface et al, 2007 as well as shown in example 13 above). We previously showed that these cytokines synergistically increased innate immunity, demonstrated by chemokine and antimicrobial peptide production. Since skin inflammation is associated with epidermal hyperplasia, we further asked for such a synergy in keratinocyte differentiation inhibition associated with acanthosis. All five cytokines separately decrease CK10 expression by NHEK between 3 to 8 fold but their combination (M5) results in a strong synergy with a 500 fold decrease of CK10 mRNA expression (FIG. 19A). These effects are more varied for other KDM. IL-22, OSM and TNFα downregulate mRNA expression of CK1, desmoglein 1 (DSG1), DSC1, FLG, CLSP, LOR and fatty acid binding protein 5 (FABPS) whereas IL-1α and IL-17A only show minor activities. In addition, a strong synergy of the M5 cytokine combination was observed for DSG1, CLSP and FLG mRNA inhibition, whereas only an additive effect of the cytokines was seen for LOR, DSC1, CK1 and FABPS (FIG. 19A). By removing a single cytokine from the M5 combination, we further identified the major contributors for keratinocyte differentiation inhibition. The absence of OSM or TNFα in the M5 partially restores the control mRNA expression of FLG, CLSP, DSG1, LOR, DSC1, CK1 and FABPS (FIG. 19B), demonstrating that OSM and TNFα were the most potent cytokines for keratinocyte differentiation inhibition. Removal of IL-22, IL-17A or IL-1α partially restores the control mRNA expression of respectively 4, 3 and 3 KDM (FIG. 19B). Finally, a kinetic study shows the confluence-induced expression of KDM during culture of unstimulated NHEK, whereas KDM expression under M5 treatment strongly and steadily decreased along culture time when compared to initial expression level (FIG. 20). In conclusion, the M5 combination displays a strong and sustained inhibition of keratinocyte differentiation. S100A7 expression under M5 stimulation was strongly induced as early as 6 h and sustained during 72 h illustrating the strong inflammatory response obtained (FIG. 20).

Activity of Proinflammatory Cytokines on RHE

In order to confirm the activity of proinflammatory cytokines in a more complete tridimensional model of epidermal differentiation, RHE have been cultured for 10 days at the air-water interface using an appropriate differentiation medium and then stimulated for 24 h or 72 h with the cytokine alone or in combination, before mRNA and protein quantification. Quantitative RT-PCR analysis confirmed that IL-22 or OSM are the most active cytokines to decrease expression of both early and late KDM such as CK10, CK1, LOR and FLG. We also observed a strong synergistic inhibitory effect of the 5 cytokines on all KDM mRNA expression (FIG. 21). IVL mRNA expression was discretely inhibited by IL-17A and by the M5, while S100A7 mRNA expression was strongly induced by OSM, IL-22 and synergistically by M5 (FIG. 21), as described in example 13 above.

If IL-1α, IL-17A or TNFα does not modify RHE histology, OSM or IL-22 induces a significant keratinocyte hyperplasia (p<0.001 and p<0.01 respectively) and a loss of keratohyalin granules in the granular layer (FIG. 22A). Immunohistological analysis confirmed that OSM or IL-22 decreases expression of CK10, LOR and FLG by RHE, whereas IL1α, IL-17A and TNFα did not exhibit any activity (FIG. 22A). On another hand, IVL expression was discreetly induced by IL-17A or TNFα, and strongly by OSM or IL-22. Finally S100A7 was strongly induced by OSM or IL-22, in a lesser extent by IL-1α and very slightly by IL-17A or TNFα. IL-22 or OSM-induced hyperplasia could not be explained by an increased keratinocyte proliferation evaluated using Ki67 staining (data not shown), in agreement with other groups and us (Boniface et al, 2005 and Sa et al, 2007), To confirm the synergy observed in NHEK, we stimulated RHE during 3 days with M5. The use of the maximum effective concentrations for each cytokine in M5 results in a complete loss of the integrity of RHE. The use of suboptimal concentrations of each cytokines in M5 (3 ng/ml) is less drastic, showing especially a disruption of the granular layers, associated with a strong inhibition of CK10, LOR, FLG and IVL expression, but sustained S100A7 expression (FIG. 22A). The effect of the M5 on RHE disorganization was not due to a direct toxicity of the cytokine mixture on keratinocytes since toxicity has neither been observed in the NHEK model (data not shown). Moreover, a JAKs inhibitor protects the integrity of the RHE and blocked the epidermal hyperplasia, demonstrating that the biological activities of the M5, especially mediated by the JAK-STAT signaling cytokines, were specifically responsible for the tissue disruption (FIG. 22B).

In Vivo Keratinocyte Differentiation Inhibition by M5 Proinflammatory Cytokines

To assess in vivo the effect of the pro-inflammatory cocktail, the M5 cytokine combination was injected intradermally into the ears of mice. After 24 h, a clear inhibition of CK1, CK10, LOR, FLG, IVL, DSG1 and DSC1 mRNA expression was observed in M5 compared to PBS-injected skin (FIG. 23A). Histological analysis performed at 48 h revealed an important epidermal hyperplasia in ears injected with M5 (FIG. 23B) Immunohistological analysis confirmed the decreased expression of CK10, LOR and FLG in M5-injected skin (FIG. 23B). In parallel, we detected in M5-injected skin a strong expression of CK6 and Ki67 staining revealing an enhanced keratinocyte proliferation under M5 stimulation.

In order to evaluate the pathophysiological relevance of our in vitro and in vivo models, we analysed the expression of several KDM in normal skin and psoriatic skin lesions. We observed a decreased CK10, LOR and FLG but increased IVL expression in psoriatic skin lesions compared to normal skin (FIG. 23C). Finally, S100A7 overexpression in psoriatic lesions was illustrated as a positive control of skin inflammation.

REFERENCES

Alowami, S., G. Qing, et al. (2003). "Psoriasin (S100A7) expression is altered during skin tumorigenesis." *BMC Dermatol* 3(1): 1.

Benigni, F., G. Fantuzzi, et al. (1996). "Six different cytokines that share GP130 as a receptor subunit, induce serum amyloid A and potentiate the induction of interleukin-6 and the activation of the hypothalamus-pituitary-adrenal axis by interleukin-1." *Blood* 87(5): 1851-4.

Bernard, F. X., N. Pedretti, et al. (2002). "Comparison of gene expression profiles in human keratinocyte monolayer cultures, reconstituted epidermis and normal human skin; transcriptional effects of retinoid treatments in reconstituted human epidermis." *Exp Dermatol* 11(1): 59-74.

Boniface K, Bernard F X, et al. (2005). "L-22 inhibits epidermal differentiation and induces proinflammatory gene expression and migration of human keratinocytes." *J Immunol.* 2005 Mar. 15; 174(6):3695-702.

Boniface, K., C. Diveu, et al. (2007). "Oncostatin M Secreted by Skin Infiltrating T Lymphocytes Is a Potent Keratinocyte Activator Involved in Skin Inflammation." *J. Immunol.* 178:4615-4622.

Bonifati, C., A. Mussi, et al. (1998). "Spontaneous release of leukemia inhibitory factor and oncostatin-M is increased in supernatants of short-term organ cultures from lesional psoriatic skin." *Arch Dermatol Res* 290(1-2): 9-13.

Boulton, T. G., N. Stahl, et al. (1994). "Ciliary neurotrophic factor/leukemia inhibitory factor/interleukin 6/oncostatin M family of cytokines induces tyrosine phosphorylation of a common set of proteins overlapping those induced by other cytokines and growth factors." *J Biol Chem* 269 (15): 11648-55.

Broome, A. M., D. Ryan, et al. (2003). "S100 protein subcellular localization during epidermal differentiation and psoriasis." *J Histochem Cytochem* 51(5): 675-85.

Bullard, K. M., L. Lund, et al. (1999). "Impaired wound contraction in stromelysin-1-deficient mice." *Ann Surg* 230(2): 260-5.

Dillon, S. R., C. Sprecher, et al. (2004). "Interleukin 31, a cytokine produced by activated T cells, induces dermatitis in mice." *Nat Immunol* 5(7): 752-60.

Donato, R. (1999). "Functional roles of S100 proteins, calcium-binding proteins of the EF-hand type." *Biochim Biophys Acta* 1450(3): 191-231.

Gallucci, R. M., P. P. Simeonova, et al. (2000). "Impaired cutaneous wound healing in interleukin-6-deficient and immunosuppressed mice." *Faseb J* 14(15): 2525-31.

Gallucci, R. M., D. K. Sloan, et al. (2004). "Interleukin 6 indirectly induces keratinocyte migration." *J Invest Dermatol* 122(3): 764-72.

Gebhardt, C., U. Breitenbach, et al. (2002). "Calgranulins S100A8 and S100A9 are negatively regulated by glucocorticoids in a c-Fos-dependent manner and overexpressed throughout skin carcinogenesis." *Oncogene* 21(27): 4266-76.

Glaser, R., J. Harder, et al. (2005). "Antimicrobial psoriasin (S100A7) protects human skin from *Escherichia coli* infection." *Nat Immunol* 6(1): 57-64.

Guenou H, Nissan X, Larcher F, Feteira J, Lemaitre G, et al. (2009) Human embryonic stem-cell derivatives for full reconstruction of the pluristratified epidermis: a preclinical study. Lancet 374: 1745-1753.

Ihn, H. and K. Tamaki (2000). "Oncostatin M stimulates the growth of dermal fibroblasts via a mitogen-activated protein kinase-dependent pathway." *J Immunol* 165(4): 2149-55.

Jonak, C., G. Klosner, et al. (2002). "Subcorneal colocalization of the small heat shock protein, hsp27, with keratins and proteins of the cornified cell envelope." *Br J Dermatol* 147(1): 13-9.

Kira, M., S. Sano, et al. (2002). "STAT3 deficiency in keratinocytes leads to compromised cell migration through hyperphosphorylation of p130(cas)." *J Biol Chem* 277(15): 12931-6.

Koch, A. E., S. L. Kunkel, et al. (1994). "Epithelial neutrophil activating peptide-78: a novel chemotactic cytokine for neutrophils in arthritis." *J Clin Invest* 94(3): 1012-8.

Komine, M., L. S. Rao, et al. (2000). "Inflammatory versus proliferative processes in epidermis. Tumor necrosis factor alpha induces K6b keratin synthesis through a transcriptional complex containing NFkappa B and C/EBP-beta." *J Biol Chem* 275(41): 32077-88.

Lugering, N., T. Kucharzik, et al. (1997). "Importance of combined treatment with IL-10 and IL-4, but not IL-13, for inhibition of monocyte release of the Ca(2+)-binding protein MRP8/14." *Immunology* 91(1): 130-4.

Madsen, P., H. H. Rasmussen, et al. (1991). "Molecular cloning, occurrence, and expression of a novel partially secreted protein "psoriasin" that is highly up-regulated in psoriatic skin." *J Invest Dermatol* 97(4): 701-12.

Mehul, B., D. Bernard, et al. (2001). "Calmodulin-like skin protein: a new marker of keratinocyte differentiation." *J Invest Dermatol* 116(6): 905-9.

Mehul, B., D. Bernard, et al. (2000). "Identification and cloning of a new calmodulin-like protein from human epidermis." *J Biol Chem* 275(17): 12841-7.

Nagase, H. and J. F. Woessner, Jr. (1999). "Matrix metalloproteinases." *J Biol Chem* 274(31): 21491-4.

Navarro, J. M., J. Casatorres, et al. (1995). "Elements controlling the expression and induction of the skin hyperproliferation-associated keratin K6." *J Biol Chem* 270(36): 21362-7.

Nizet, V., T. Ohtake, et al. (2001). "Innate antimicrobial peptide protects the skin from invasive bacterial infection." *Nature* 414(6862): 454-7.

Nomura, I., E. Goleva, et al. (2003). "Cytokine milieu of atopic dermatitis, as compared to psoriasis, skin prevents induction of innate immune response genes." *J Immunol* 171(6): 3262-9.

Ong, P. Y., T. Ohtake, et al. (2002). "Endogenous antimicrobial peptides and skin infections in atopic dermatitis." *N Engl J Med* 347(15): 1151-60.

Paglia, D., S. Kondo, et al. (1996). "Leukaemia inhibitory factor is expressed by normal human keratinocytes in vitro and in vivo." *Br J Dermatol* 134(5): 817-23.

Paramio, J. M., M. L. Casanova, et al. (1999). "Modulation of cell proliferation by cytokeratins K10 and K16." *Mol Cell Biol* 19(4): 3086-94.

Pattyn, F., F. Speleman, et al. (2003). "RTPrimerDB: the real-time PCR primer and probe database." *Nucleic Acids Res* 31(1): 122-3.

Pfaffl, M. W. (2001). "A new mathematical model for relative quantification in real-time RT-PCR." *Nucleic Acids Res* 29(9): e45.

Pfaffl, M. W., G. W. Horgan, and L. Dempfle. (2002). "Relative expression software tool (REST) for group-wise comparison and statistical analysis of relative expression results in real-time PCR". *Nucleic Acids Res* 30:e36.

Pilcher, B. K., M. Wang, et al. (1999). "Role of matrix metalloproteinases and their inhibition in cutaneous wound healing and allergic contact hypersensitivity." *Ann N Y Acad Sci* 878: 12-24.

Rogers, M. S., T. Kobayashi, et al. (2001). "Human calmodulin-like protein is an epithelial-specific protein regulated during keratinocyte differentiation." *Exp Cell Res* 267(2): 216-24.

Rollman, O., U. B. Jensen, et al. (2003). "Platelet derived growth factor (PDGF) responsive epidermis formed from human keratinocytes transduced with the PDGF beta receptor gene." *J Invest Dermatol* 120(5): 742-9.

Rosdy, M., B. Bertino, et al. (1997). "Retinoic acid inhibits epidermal differentiation when applied topically on the stratum corneum of epidermis formed in vitro by human keratinocytes grown on defined medium." *In Vitro Toxicology* 10(1): 39-47.

Roth, J., T. Vogl, et al. (2003). "Phagocyte-specific S100 proteins: a novel group of proinflammatory molecules." *Trends Immunol* 24(4): 155-8.

Ryckman, C., K. Vandal, et al. (2003). "Proinflammatory activities of S100: proteins S100A8, S100A9, and S100A8/A9 induce neutrophil chemotaxis and adhesion." *J Immunol* 170(6): 3233-42.

Sa S M, Valdez P A, Wu J, Jung K, Zhong F, et al. (2007) The effects of IL-20 subfamily cytokines on reconstituted human epidermis suggest potential roles in cutaneous innate defense and pathogenic adaptive immunity in psoriasis. J Immunol 178: 2229-2240. Harder, J., J. Bartels, et al. (1997). "A peptide antibiotic from human skin."

*Nature* 387(6636): 861. Sano, S., S. Itami, et al. (1999). "Keratinocyte-specific ablation of Stat3 exhibits impaired skin remodeling, but does not affect skin morphogenesis." *Embo J* 18(17): 4657-68.

Sugawara, T., R. M. Gallucci, et al. (2001). "Regulation and role of interleukin 6 in wounded human epithelial keratinocytes." *Cytokine* 15(6): 328-36.

Taga, T. and T. Kishimoto (1997). "Gp130 and the interleukin-6 family of cytokines." *Annu Rev Immunol* 15: 797-819.

Thorey, I. S., J. Roth, et al. (2001). "The Ca2+-binding proteins S100A8 and S100A9 are encoded by novel injury-regulated genes." *J Biol Chem* 276(38): 35818-25.

Vandesompele, J., K. De Preter, et al. (2002). "Accurate normalization of real-time quantitative RT-PCR data by geometric averaging of multiple internal control genes." *Genome Biol* 3(7): RESEARCH0034.

Wagener, F. A., H. E. van Beurden, et al. (2003). "The heme-heme oxygenase system: a molecular switch in wound healing." *Blood* 102(2): 521-8.

Wahl, A. F. and P. M. Wallace (2001). "Oncostatin M in the anti-inflammatory response." *Ann Rheum Dis* 60 Suppl 3: iii75-80.

Watson, P. H., E. R. Leygue, et al. (1998). "Psoriasin (S100A7)." *Int J Biochem Cell Biol* 30(5): 567-71.

That which is claimed:

1. A method for stimulating an increase in the expression of anti-microbial peptides selected from the group consisting of cathelicidins, defensins, S100 calcium-binding proteins, Wey Acidic Protein Four-Disulfide Core Domain proteins (WFDC) and RNAse 7, by keratinocytes in vitro by culturing said keratinocytes in presence with a composition comprising IL-17, TNFα and Oncostatin M (OSM) or in vivo by contacting said keratinocytes topically or intradermally in a subject suffering from acne, atopic dermatitis, eczema, seborrheic dermatitis, erythema, eschar, skin ulcers, ichtyosis, bullous epidermolysis, malum perforans pedis, wart, with an effective amount of a composition comprising IL-17, TNFα and Oncostatin M (OSM), said expression of anti-microbial peptides being increased in comparison with unstimulated keratinocytes.

2. The method according to claim 1, wherein said anti-microbial peptides are chosen from:

cathelicidin LL37, beta-defensin 2 and beta-defensin 3,

S100 calcium-binding protein A7, S100 calcium-binding protein A7A, S100 calcium-binding protein A8, S100 calcium-binding protein A9, S100 calcium-binding protein A12, Wey Acidic Protein Four-Disulfide Core Domain protein (WFDC5) and Wey Acidic Protein Four-Disulfide Core Domain protein 12 (WFDC12), and RNAse 7.

* * * * *

UNITED STATES PATENT AND TRADEMARK OFFICE
CERTIFICATE OF CORRECTION

PATENT NO. : 10,080,779 B2  
APPLICATION NO. : 14/500373  
DATED : September 25, 2018  
INVENTOR(S) : Lecron et al.

Page 1 of 1

It is certified that error appears in the above-identified patent and that said Letters Patent is hereby corrected as shown below:

In the Claims

<u>Column 42,</u>
Lines 28 and 29, "protein (WFDC5)" should read --protein 5 (WFDC5)--.

Signed and Sealed this
Nineteenth Day of February, 2019

Andrei Iancu
*Director of the United States Patent and Trademark Office*

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: forward primer for reverse transcription of
      OSMR

<400> SEQUENCE: 1
cctgcctacc tgaaaaccag                                              20

<210> SEQ ID NO 2
<211> LENGTH: 20
<212> TYPE: DNA
<213> ORGANISM: Artificial
<220> FEATURE:
<223> OTHER INFORMATION: reverse primer for reverse transcription of
      OSMR

<400> SEQUENCE: 2
acattggtgc cttcttccac                                              20

<210> SEQ ID NO 3
<211> LENGTH: 22
<212> TYPE: DNA
<213> ORGANISM: Artificial
<220> FEATURE:
<223> OTHER INFORMATION: forward primer for reverse transcription of
      gp130

<400> SEQUENCE: 3
gggcaatatg actctttgaa gg                                           22

<210> SEQ ID NO 4
<211> LENGTH: 22
<212> TYPE: DNA
<213> ORGANISM: Artificial
<220> FEATURE:
<223> OTHER INFORMATION: reverse primer for reverse transcription of
      gp130

<400> SEQUENCE: 4
ttcctgttga tgttcagaat gg                                           22

<210> SEQ ID NO 5
<211> LENGTH: 20
<212> TYPE: DNA
<213> ORGANISM: Artificial
<220> FEATURE:
<223> OTHER INFORMATION: forward primer for reverse transcription of
      LIFR
```

```
<400> SEQUENCE: 5
cagtacaaga gcagcggaat                                               20

<210> SEQ ID NO 6
<211> LENGTH: 20
<212> TYPE: DNA
<213> ORGANISM: Artificial
<220> FEATURE:
<223> OTHER INFORMATION: reverse primer for reverse transcription of
      LIFR

<400> SEQUENCE: 6
ccagtccata aggcatggtt                                               20

<210> SEQ ID NO 7
<211> LENGTH: 20
<212> TYPE: DNA
<213> ORGANISM: Artificial
<220> FEATURE:
<223> OTHER INFORMATION: forward primer for reverse transcription of
      GAPDH

<400> SEQUENCE: 7
accacagtcc atgccatcac                                               20

<210> SEQ ID NO 8
<211> LENGTH: 20
<212> TYPE: DNA
<213> ORGANISM: Artificial
<220> FEATURE:
<223> OTHER INFORMATION: reverse primer for reverse transcription of
      GAPDH

<400> SEQUENCE: 8
tccaccaccc tgttgctgta                                               20

<210> SEQ ID NO 9
<211> LENGTH: 28
<212> TYPE: DNA
<213> ORGANISM: Artificial
<220> FEATURE:
<223> OTHER INFORMATION: forward primer for Q-RT-PCR of S100A7

<400> SEQUENCE: 9
gcatgatcga catgtttcac aaatacac                                      28

<210> SEQ ID NO 10
<211> LENGTH: 23
<212> TYPE: DNA
<213> ORGANISM: Artificial
<220> FEATURE:
<223> OTHER INFORMATION: reverse primer for Q-RT-PCR of S100A7

<400> SEQUENCE: 10
tggtagtctg tggctatgtc tcc                                           23

<210> SEQ ID NO 11
<211> LENGTH: 26
<212> TYPE: DNA
<213> ORGANISM: Artificial
<220> FEATURE:
<223> OTHER INFORMATION: forward primer for Q-RT-PCR of S100A9

<400> SEQUENCE: 11
gctcctcggc tttgacagag tgcaag                                        26
```

<210> SEQ ID NO 12
<211> LENGTH: 30
<212> TYPE: DNA
<213> ORGANISM: Artificial
<220> FEATURE:
<223> OTHER INFORMATION: reverse primer for Q-RT-PCR of S100A9

<400> SEQUENCE: 12
gcatttgtgt ccaggtcctc catgatgtgt                              30

<210> SEQ ID NO 13
<211> LENGTH: 22
<212> TYPE: DNA
<213> ORGANISM: Artificial
<220> FEATURE:
<223> OTHER INFORMATION: forward primer for Q-RT-PCR of hBD2/4

<400> SEQUENCE: 13
gccatcagcc atgagggtct tg                                      22

<210> SEQ ID NO 14
<211> LENGTH: 21
<212> TYPE: DNA
<213> ORGANISM: Artificial
<220> FEATURE:
<223> OTHER INFORMATION: reverse primer for Q-RT-PCR of hBD2/4

<400> SEQUENCE: 14
aatccgcatc agccacagca g                                       21

<210> SEQ ID NO 15
<211> LENGTH: 20
<212> TYPE: DNA
<213> ORGANISM: Artificial
<220> FEATURE:
<223> OTHER INFORMATION: forward primer for Q-RT-PCR of KRT10

<400> SEQUENCE: 15
gcccgacggt agagttcttt                                         20

<210> SEQ ID NO 16
<211> LENGTH: 21
<212> TYPE: DNA
<213> ORGANISM: Artificial
<220> FEATURE:
<223> OTHER INFORMATION: reverse primer for Q-RT-PCR of KRT10

<400> SEQUENCE: 16
cagaaaccac aaaacacctt g                                       21

<210> SEQ ID NO 17
<211> LENGTH: 20
<212> TYPE: DNA
<213> ORGANISM: Artificial
<220> FEATURE:
<223> OTHER INFORMATION: forward primer for Q-RT-PCR of OSM

<400> SEQUENCE: 17
tcagtctggt ccttgcactc                                         20

<210> SEQ ID NO 18
<211> LENGTH: 20
<212> TYPE: DNA
<213> ORGANISM: Artificial
<220> FEATURE:

<223> OTHER INFORMATION: reverse primer for Q-RT-PCR of OSM

<400> SEQUENCE: 18
ctgcagtgct ctctcagttt    20

<210> SEQ ID NO 19
<211> LENGTH: 19
<212> TYPE: DNA
<213> ORGANISM: Artificial
<220> FEATURE:
<223> OTHER INFORMATION: forward primer for Q-RT-PCR of GAPDH

<400> SEQUENCE: 19
gaaggtgaag gtcggagtc    19

<210> SEQ ID NO 20
<211> LENGTH: 20
<212> TYPE: DNA
<213> ORGANISM: Artificial
<220> FEATURE:
<223> OTHER INFORMATION: reverse primer for Q-RT-PCR of GAPDH

<400> SEQUENCE: 20
gaagatggtg atgggatttc    20

<210> SEQ ID NO 21
<211> LENGTH: 22
<212> TYPE: DNA
<213> ORGANISM: Artificial
<220> FEATURE:
<223> OTHER INFORMATION: forward primer for Q-RT-PCR of murine S100A8

<400> SEQUENCE: 21
tccaatatac aaggaaatca cc    22

<210> SEQ ID NO 22
<211> LENGTH: 18
<212> TYPE: DNA
<213> ORGANISM: Artificial
<220> FEATURE:
<223> OTHER INFORMATION: reverse primer for Q-RT-PCR of murine S100A8

<400> SEQUENCE: 22
tttatcacca tcgcaagg    18

<210> SEQ ID NO 23
<211> LENGTH: 20
<212> TYPE: DNA
<213> ORGANISM: Artificial
<220> FEATURE:
<223> OTHER INFORMATION: forward primer for Q-RT-PCR of murine S100A9

<400> SEQUENCE: 23
gaaggaattc agacaaatgg    20

<210> SEQ ID NO 24
<211> LENGTH: 18
<212> TYPE: DNA
<213> ORGANISM: Artificial
<220> FEATURE:
<223> OTHER INFORMATION: reverse primer for Q-RT-PCR of murine S100A9

<400> SEQUENCE: 24
atcaactttg ccatcagc    18

```
<210> SEQ ID NO 25
<211> LENGTH: 19
<212> TYPE: DNA
<213> ORGANISM: Artificial
<220> FEATURE:
<223> OTHER INFORMATION: forward primer for Q-RT-PCR of murine MIP-1
      beta

<400> SEQUENCE: 25
cctctctctc ctcttgctc                                                    19

<210> SEQ ID NO 26
<211> LENGTH: 20
<212> TYPE: DNA
<213> ORGANISM: Artificial
<220> FEATURE:
<223> OTHER INFORMATION: reverse primer for Q-RT-PCR of murine MIP-1
      beta

<400> SEQUENCE: 26
agatctgtct gcctcttttg                                                   20

<210> SEQ ID NO 27
<211> LENGTH: 18
<212> TYPE: DNA
<213> ORGANISM: Artificial
<220> FEATURE:
<223> OTHER INFORMATION: forward primer for Q-RT-PCR of murine MDC

<400> SEQUENCE: 27
tgctgccagg actacatc                                                     18

<210> SEQ ID NO 28
<211> LENGTH: 19
<212> TYPE: DNA
<213> ORGANISM: Artificial
<220> FEATURE:
<223> OTHER INFORMATION: reverse primer for Q-RT-PCR of murine MDC

<400> SEQUENCE: 28
tagcttcttc acccagacc                                                    19

<210> SEQ ID NO 29
<211> LENGTH: 20
<212> TYPE: DNA
<213> ORGANISM: Artificial
<220> FEATURE:
<223> OTHER INFORMATION: forward primer for Q-RT-PCR of murine TARC

<400> SEQUENCE: 29
cattcctatc aggaagttgg                                                   20

<210> SEQ ID NO 30
<211> LENGTH: 19
<212> TYPE: DNA
<213> ORGANISM: Artificial
<220> FEATURE:
<223> OTHER INFORMATION: reverse primer for Q-RT-PCR of murine TARC

<400> SEQUENCE: 30
cttgggtttt tcaccaatc                                                    19

<210> SEQ ID NO 31
<211> LENGTH: 19
<212> TYPE: DNA
<213> ORGANISM: Artificial
<220> FEATURE:
```

```
<223> OTHER INFORMATION: forward primer for Q-RT-PCR of murine GAPDH

<400> SEQUENCE: 31
atcaagaagg tggtgaagc                                                19

<210> SEQ ID NO 32
<211> LENGTH: 20
<212> TYPE: DNA
<213> ORGANISM: Artificial
<220> FEATURE:
<223> OTHER INFORMATION: reverse primer for Q-RT-PCR of murine GAPDH

<400> SEQUENCE: 32
gccgtattca ttgtcatacc                                               20
```